US012643934B2

(12) United States Patent
Peakman et al.

(10) Patent No.: US 12,643,934 B2
(45) Date of Patent: Jun. 2, 2026

(54) PROINSULIN PEPTIDES FOR TYPE 1 DIABETES

(71) Applicant: King's College London, Greater London (GB)

(72) Inventors: Mark Peakman, Greater London (GB); Johan Verhagen, Greater London (GB); Martin Eichmann, Greater London (GB)

(73) Assignee: King's College London, Greater London (GB)

( * ) Notice: Subject to any disclaimer, the term of this patent is extended or adjusted under 35 U.S.C. 154(b) by 1071 days.

(21) Appl. No.: 17/761,151

(22) PCT Filed: Sep. 16, 2020

(86) PCT No.: PCT/GB2020/052236
§ 371 (c)(1),
(2) Date: Mar. 16, 2022

(87) PCT Pub. No.: WO2021/053331
PCT Pub. Date: Mar. 25, 2021

(65) Prior Publication Data
US 2023/0348562 A1 Nov. 2, 2023

(30) Foreign Application Priority Data

Sep. 17, 2019 (GB) ..................................... 1913408

(51) Int. Cl.
| | |
|---|---|
| *A61K 38/10* | (2006.01) |
| *A61K 9/14* | (2006.01) |
| *A61K 31/198* | (2006.01) |
| *A61K 38/28* | (2006.01) |
| *A61K 39/00* | (2006.01) |
| *A61P 3/10* | (2006.01) |
| *C07K 14/625* | (2006.01) |
| *C07K 14/705* | (2006.01) |
| *G01N 33/50* | (2006.01) |
| *G01N 33/569* | (2006.01) |

(52) U.S. Cl.
CPC ........ *C07K 14/70532* (2013.01); *A61K 9/146* (2013.01); *A61K 31/198* (2013.01); *G01N 33/56977* (2013.01); *G01N 2800/042* (2013.01); *G01N 2800/50* (2013.01)

(58) Field of Classification Search
CPC .. C07K 14/70532; C07K 14/62; A61K 9/146; A61K 31/198; A61K 38/10; G01N 33/56977; G01N 2800/042; G01N 2333/62; G01N 33/505; G01N 33/74; A61P 3/10
See application file for complete search history.

(56) References Cited

FOREIGN PATENT DOCUMENTS

| | | |
|---|---|---|
| JP | 2016528254 A | 9/2016 |
| WO | 2006007667 A1 | 1/2006 |
| WO | 2012041968 | 4/2012 |
| WO | 2014160465 | 10/2014 |
| WO | 2016081869 A2 | 5/2016 |
| WO | 2016198887 | 12/2016 |
| WO | 2017112899 | 6/2017 |
| WO | 2015023796 | 2/2019 |
| WO | 2019050465 | 3/2019 |
| WO | 2019104391 A1 | 6/2019 |

OTHER PUBLICATIONS

Uniprot Accession F6MZK5, human precursor insulin, accessed Sep. 17, 2025 at URL uniprot.org/uniprotkb/F6MZK5, pp. 1-7 (2025) (Year: 2025).*
Pociot et al., "Type 1 Diabetes—Genetic risk factors for type 1 diabetes," Lancet 387: 2331-39 (2016) (Year: 2016).*
Type 1 diabetes, CDC, accessed Sep. 17, 2025 at URL cdc.gov/diabetes/about/about-type-1-diabetes.html, pp. 1-3 (Year: 2025).*
Kanduc D, "Homology, similarity, and identity in peptide epitope immunodefinition," Journal of Peptide Science, 18: 487-494 (Year: 2012).*
Person, "An Introduction to Sequence Similarity ("Homology") Searching," Current Protocols in Bioinformatics, 3.1.1-3.1.8. (Year: 2013).*
Drumm et al, Genetic Variation and Clinical Heterogeneity in Cystic Fibrosis, Annu. Rev. Pathol. Mech. Dis., Jul. 2012, pp. 267-282 (Year: 2012).*
Yampolsky et al, The Exchangeability of Amino Acids in Proteins, Genetics, 2005, 170, pp. 1459-1472. (Year: 2005).*
Van Lummel et al, "Posttranslational Modification of HLA-DQ Binding Islet Autoantigens in Type 1 Diabetes," Diabetes 63:237-247 (2014) (Year: 2014).*
McLaughlin et al., "Human islets and dendritic cells generate post-translationally modified islet autoantigens," Clinical experimental immunology 185: 1 33-140 (2016) (Year: 2016).*
ISA; International Search Report and Written Opinion dated Mar. 25, 2021 in PCT/GB2020/052236.
Geluk, A. et al., "HLA-DR binding analysis of peptides from islet antigens in IDDM", Diabetes, 1998, vol. 47, pp. 1594-1601.
Schloot, N. C. et al., "Molecular mimicry in type 1 diabetes mellitus revisited: T-cell clones to GAD65 peptides with sequence homology to Coxsackie or proinsulin peptides do not crossreact with homologous counterpart", Human Immunology, 2001, vol. 62, pp. 299-309.

* cited by examiner

*Primary Examiner* — Julie Ha
*Assistant Examiner* — Kristina M Hellman
(74) *Attorney, Agent, or Firm* — Haynes and Boone, LLP

(57) ABSTRACT

Disclosed herein is a peptide that can be used in the therapy or prevention of Type 1 Diabetes (T1D), particularly in a patient with a DR3-DQ2 haplotype, as well as methods of diagnosing or determining treatment efficacy, methods of identifying T1D-relevant antigen drivers, and to methods of identifying subjects as being at high-risk of T1D and patients as being suitable for and/or responsive to T1D treatment.

Figure 1:
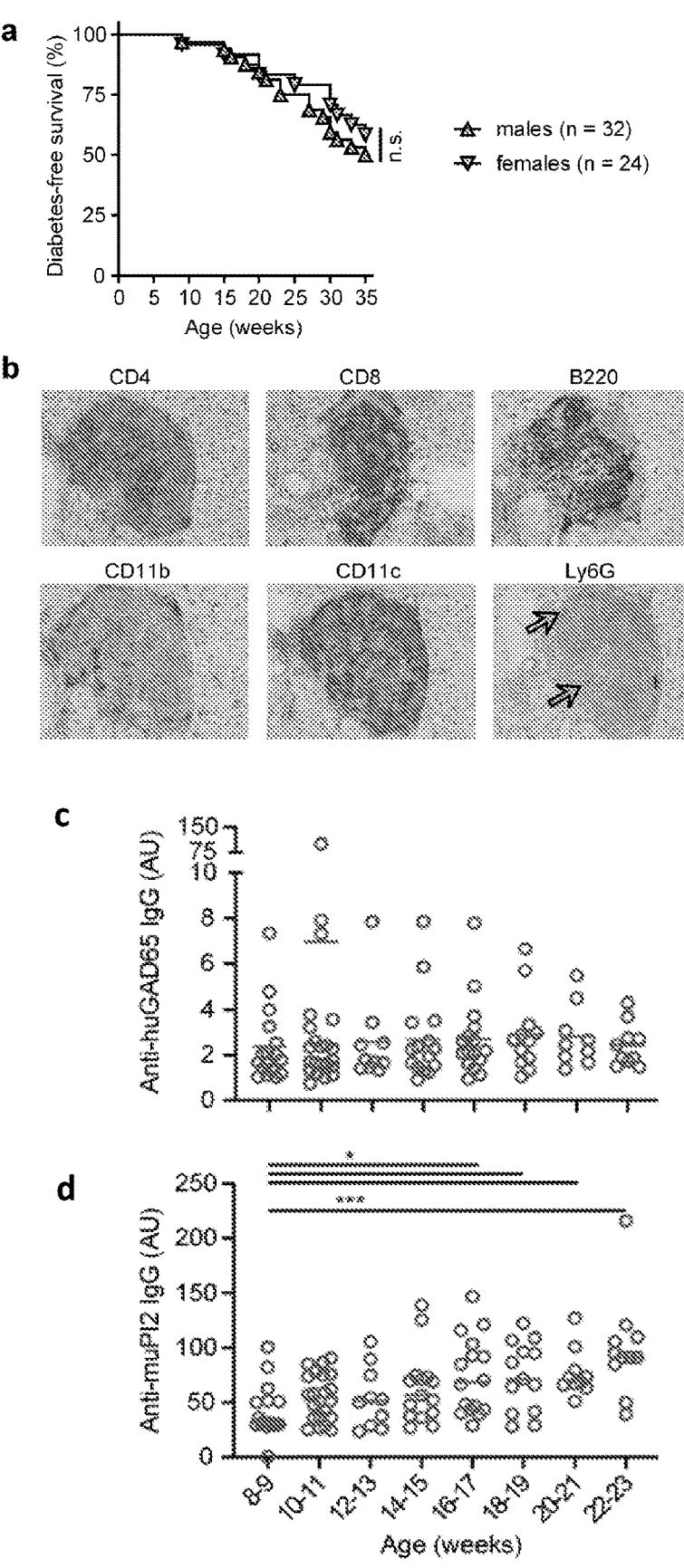

11 Claims, 9 Drawing Sheets
Specification includes a Sequence Listing.

Figure 4 a

|  | B chain | C peptide |  |
|---|---|---|---|
| Human | GFFYTPKTRREAEDLQVGQVELGGGPGAGS | (SEQ ID NO: 5) |
| Mouse | GFFYTPMSRREVEDPQVAQLELGGGPGAGD | (SEQ ID NO: 6) |

GP-15 (SEQ ID NO: 7)    GFFYTPMSRREVEDP

YA-15 (SEQ ID NO: 8)        YTPMSRREVEDPQVA

ME-15 (SEQ ID NO: 9)            MSRREVEDPQVAQLE

RG-15 (SEQ ID NO: 10)               REVEDPQVAQLELGG

DA-15 (SEQ ID NO: 11)                    DPQVAQLELGGGPGA

VD-14 (SEQ ID NO: 12)                        VAQLELGGGPGAGD b

| Peptide | SEQ ID NO: | HLA-DR3 | | | HLA-DQ2 | | |
|---|---|---|---|---|---|---|---|
| | | Core | SEQ ID NO: | IC50 (nM) | Core | SEQ ID NO: | IC50 (nM) |
| GFFYTPMSRREVEDP | 7 | FFYTPMSRR | 17 | 490.26 | FFYTPMSRR | 17 | 3959.45 |
| YTPMSRREVEDPQVA | 8 | REVEDPQVA | 18 | 14204.88 | MSRREVEDP | 22 | 3737.37 |
| MSRREVEDPQVAQLE | 9 | EVEDPQVAQ | 19 | 7011.58 | EDPQVAQLE | 23 | 1306.68 |
| REVEDPQVAQLELGG | 10 | EVEDPQVAQ | 19 | 8436.52 | EDPQVAQLE | 23 | 1040.49 |
| DPQVAQLELGGGPGA | 11 | PQVAQLELG | 20 | 19605.27 | PQVAQLELG | 20 | 7097.60 |
| (Q)VAQLELGGGPGAGD | 12 | LELGGGPGA | 21 | 23175.96 | LELGGGPGA | 21 | 16095.38 | c

| Peptide | SEQ ID NO: | HLA-DR3 | | | HLA-DQ2 | | |
|---|---|---|---|---|---|---|---|
| | | Core | SEQ ID NO: | IC50 (nM) | Core | SEQ ID NO: | IC50 (nM) |
| GFFYTPKTRREAEDL | 13 | FFYTPKTRR | 24 | 341.18 | KTRREAEDL | 29 | 7594.00 |
| YTPKTRREAEDLQVG | 14 | TRREAEDLQ | 25 | 12139.06 | TRREAEDLQ | 25 | 2681.41 |
| KTRREAEDLQVGQVE | 2 | EAEDLQVGQ | 26 | 10335.91 | EDLQVGQVE | 30 | 1069.04 |
| REAEDLQVGQVELGG | 3 | LQVGQVELG | 27 | 6776.19 | EDLQVGQVE | 30 | 1073.75 |
| DLQVGQVELGGGPGA | 15 | LQVGQVELG | 27 | 10940.62 | LQVGQVELG | 27 | 6190.23 |
| (Q)VGQVELGGGPGAGS | 16 | VELGGGPGA | 28 | 25844.08 | VELGGGPGA | 28 | 18725.77 |

Figure 5
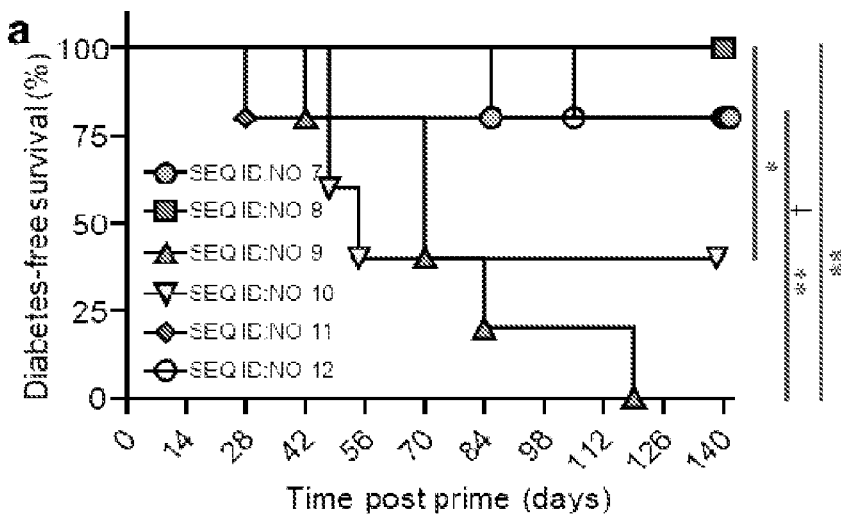
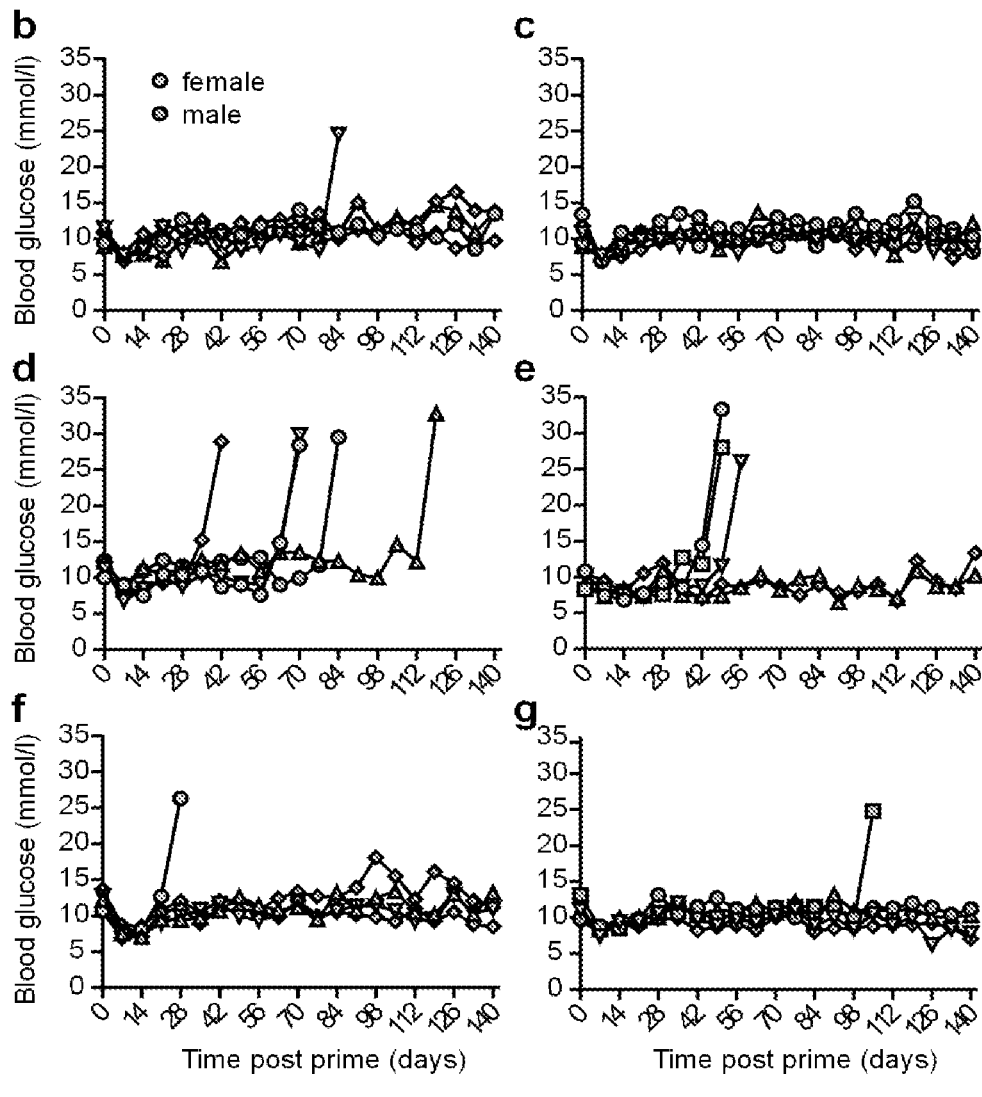

Figure 6
a
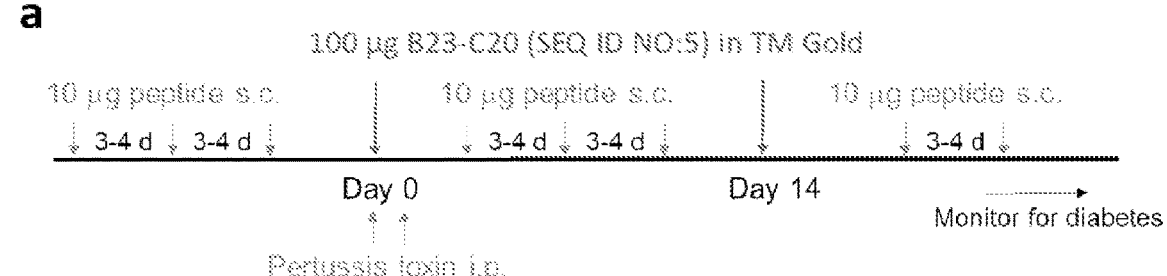
b
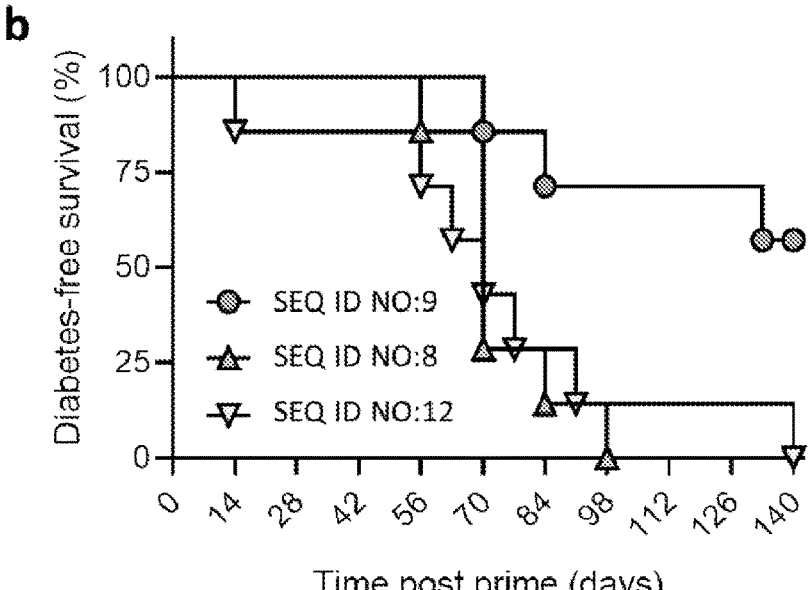

Figure 8B

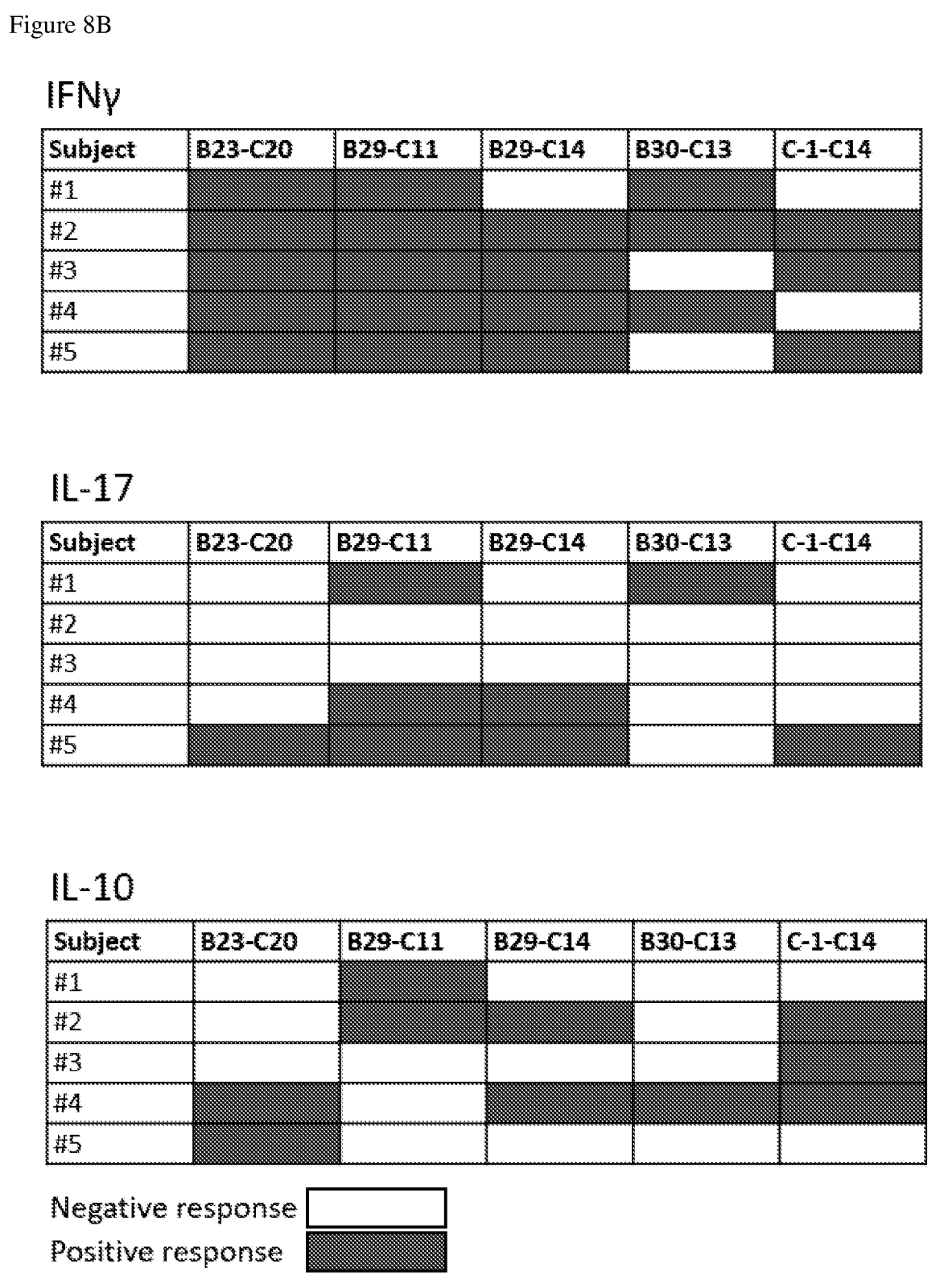

IFNγ

| Subject | B23-C20 | B29-C11 | B29-C14 | B30-C13 | C-1-C14 |
|---|---|---|---|---|---|
| #1 | Positive | Positive | Negative | Positive | Negative |
| #2 | Positive | Positive | Positive | Positive | Positive |
| #3 | Positive | Positive | Positive | Negative | Positive |
| #4 | Positive | Positive | Positive | Positive | Negative |
| #5 | Positive | Positive | Positive | Negative | Positive |

IL-17

| Subject | B23-C20 | B29-C11 | B29-C14 | B30-C13 | C-1-C14 |
|---|---|---|---|---|---|
| #1 | Negative | Positive | Negative | Positive | Negative |
| #2 | Negative | Negative | Negative | Negative | Negative |
| #3 | Negative | Negative | Negative | Negative | Negative |
| #4 | Negative | Positive | Positive | Negative | Negative |
| #5 | Positive | Positive | Positive | Negative | Positive |

IL-10

| Subject | B23-C20 | B29-C11 | B29-C14 | B30-C13 | C-1-C14 |
|---|---|---|---|---|---|
| #1 | Negative | Positive | Negative | Negative | Negative |
| #2 | Negative | Positive | Positive | Negative | Positive |
| #3 | Negative | Negative | Positive | Negative | Positive |
| #4 | Positive | Negative | Positive | Positive | Positive |
| #5 | Positive | Negative | Negative | Negative | Negative |

Negative response ☐
Positive response ▓

SEQUENCE LISTING

<160> NUMBER OF SEQ ID NOS: 49

<210> SEQ ID NO 1
<211> LENGTH: 16
<212> TYPE: PRT
<213> ORGANISM: Homo sapiens

<400> SEQUENCE: 1

Thr Arg Arg Glu Ala Glu Asp Leu Gln Val Gly Gln Val Glu Leu Gly
1               5                   10                  15

<210> SEQ ID NO 2
<211> LENGTH: 15
<212> TYPE: PRT
<213> ORGANISM: Homo sapiens

<400> SEQUENCE: 2

Lys Thr Arg Arg Glu Ala Glu Asp Leu Gln Val Gly Gln Val Glu
1               5                   10                  15

<210> SEQ ID NO 3
<211> LENGTH: 15
<212> TYPE: PRT
<213> ORGANISM: Homo sapiens

<400> SEQUENCE: 3

Arg Glu Ala Glu Asp Leu Gln Val Gly Gln Val Glu Leu Gly Gly
1               5                   10                  15

<210> SEQ ID NO 4
<211> LENGTH: 18
<212> TYPE: PRT
<213> ORGANISM: Homo sapiens

<400> SEQUENCE: 4

Lys Thr Arg Arg Glu Ala Glu Asp Leu Gln Val Gly Gln Val Glu Leu
1               5                   10                  15

Gly Gly

<210> SEQ ID NO 5
<211> LENGTH: 30
<212> TYPE: PRT
<213> ORGANISM: Homo sapiens

<400> SEQUENCE: 5

Gly Phe Phe Tyr Thr Pro Lys Thr Arg Arg Glu Ala Glu Asp Leu Gln
1               5                   10                  15

Val Gly Gln Val Glu Leu Gly Gly Gly Pro Gly Ala Gly Ser
            20                  25                  30

<210> SEQ ID NO 6
<211> LENGTH: 30

-continued

```
<212> TYPE: PRT
<213> ORGANISM: Mus musculus

<400> SEQUENCE: 6

Gly Phe Phe Tyr Thr Pro Met Ser Arg Arg Glu Val Glu Asp Pro Gln
1               5                   10                  15

Val Ala Gln Leu Glu Leu Gly Gly Gly Pro Gly Ala Gly Asp
            20                  25                  30

<210> SEQ ID NO 7
<211> LENGTH: 15
<212> TYPE: PRT
<213> ORGANISM: Mus musculus

<400> SEQUENCE: 7

Gly Phe Phe Tyr Thr Pro Met Ser Arg Arg Glu Val Glu Asp Pro
1               5                   10                  15

<210> SEQ ID NO 8
<211> LENGTH: 15
<212> TYPE: PRT
<213> ORGANISM: Mus musculus

<400> SEQUENCE: 8

Tyr Thr Pro Met Ser Arg Arg Glu Val Glu Asp Pro Gln Val Ala
1               5                   10                  15

<210> SEQ ID NO 9
<211> LENGTH: 15
<212> TYPE: PRT
<213> ORGANISM: Mus musculus

<400> SEQUENCE: 9

Met Ser Arg Arg Glu Val Glu Asp Pro Gln Val Ala Gln Leu Glu
1               5                   10                  15

<210> SEQ ID NO 10
<211> LENGTH: 15
<212> TYPE: PRT
<213> ORGANISM: Mus musculus

<400> SEQUENCE: 10

Arg Glu Val Glu Asp Pro Gln Val Ala Gln Leu Glu Leu Gly Gly
1               5                   10                  15

<210> SEQ ID NO 11
<211> LENGTH: 15
<212> TYPE: PRT
<213> ORGANISM: Mus musculus

<400> SEQUENCE: 11

Asp Pro Gln Val Ala Gln Leu Glu Leu Gly Gly Gly Pro Gly Ala
1               5                   10                  15

<210> SEQ ID NO 12
<211> LENGTH: 14
<212> TYPE: PRT
<213> ORGANISM: Mus musculus

<400> SEQUENCE: 12

Val Ala Gln Leu Glu Leu Gly Gly Gly Pro Gly Ala Gly Asp
1               5                   10

<210> SEQ ID NO 13
```

<211> LENGTH: 15
<212> TYPE: PRT
<213> ORGANISM: Homo sapiens

<400> SEQUENCE: 13

Gly Phe Phe Tyr Thr Pro Lys Thr Arg Arg Glu Ala Glu Asp Leu
1               5                   10                  15

<210> SEQ ID NO 14
<211> LENGTH: 15
<212> TYPE: PRT
<213> ORGANISM: Homo sapiens

<400> SEQUENCE: 14

Tyr Thr Pro Lys Thr Arg Arg Glu Ala Glu Asp Leu Gln Val Gly
1               5                   10                  15

<210> SEQ ID NO 15
<211> LENGTH: 15
<212> TYPE: PRT
<213> ORGANISM: Homo sapiens

<400> SEQUENCE: 15

Asp Leu Gln Val Gly Gln Val Glu Leu Gly Gly Gly Pro Gly Ala
1               5                   10                  15

<210> SEQ ID NO 16
<211> LENGTH: 14
<212> TYPE: PRT
<213> ORGANISM: Homo sapiens

<400> SEQUENCE: 16

Val Gly Gln Val Glu Leu Gly Gly Gly Pro Gly Ala Gly Ser
1               5                   10

<210> SEQ ID NO 17
<211> LENGTH: 9
<212> TYPE: PRT
<213> ORGANISM: Mus musculus

<400> SEQUENCE: 17

Phe Phe Tyr Thr Pro Met Ser Arg Arg
1               5

<210> SEQ ID NO 18
<211> LENGTH: 9
<212> TYPE: PRT
<213> ORGANISM: Mus musculus

<400> SEQUENCE: 18

Arg Glu Val Glu Asp Pro Gln Val Ala
1               5

<210> SEQ ID NO 19
<211> LENGTH: 9
<212> TYPE: PRT
<213> ORGANISM: Mus musculus

<400> SEQUENCE: 19

Glu Val Glu Asp Pro Gln Val Ala Gln
1               5

<210> SEQ ID NO 20
<211> LENGTH: 9
<212> TYPE: PRT

-continued

<213> ORGANISM: Mus musculus

<400> SEQUENCE: 20

Pro Gln Val Ala Gln Leu Glu Leu Gly
1               5

<210> SEQ ID NO 21
<211> LENGTH: 9
<212> TYPE: PRT
<213> ORGANISM: Mus musculus

<400> SEQUENCE: 21

Leu Glu Leu Gly Gly Gly Pro Gly Ala
1               5

<210> SEQ ID NO 22
<211> LENGTH: 9
<212> TYPE: PRT
<213> ORGANISM: Mus musculus

<400> SEQUENCE: 22

Met Ser Arg Arg Glu Val Glu Asp Pro
1               5

<210> SEQ ID NO 23
<211> LENGTH: 9
<212> TYPE: PRT
<213> ORGANISM: Mus musculus

<400> SEQUENCE: 23

Glu Asp Pro Gln Val Ala Gln Leu Glu
1               5

<210> SEQ ID NO 24
<211> LENGTH: 9
<212> TYPE: PRT
<213> ORGANISM: Homo sapiens

<400> SEQUENCE: 24

Phe Phe Tyr Thr Pro Lys Thr Arg Arg
1               5

<210> SEQ ID NO 25
<211> LENGTH: 9
<212> TYPE: PRT
<213> ORGANISM: Homo sapiens

<400> SEQUENCE: 25

Thr Arg Arg Glu Ala Glu Asp Leu Gln
1               5

<210> SEQ ID NO 26
<211> LENGTH: 9
<212> TYPE: PRT
<213> ORGANISM: Homo sapiens

<400> SEQUENCE: 26

Glu Ala Glu Asp Leu Gln Val Gly Gln
1               5

<210> SEQ ID NO 27
<211> LENGTH: 9
<212> TYPE: PRT
<213> ORGANISM: Homo sapiens

```
<400> SEQUENCE: 27

Leu Gln Val Gly Gln Val Glu Leu Gly
1               5

<210> SEQ ID NO 28
<211> LENGTH: 9
<212> TYPE: PRT
<213> ORGANISM: Homo sapiens

<400> SEQUENCE: 28

Val Glu Leu Gly Gly Gly Pro Gly Ala
1               5

<210> SEQ ID NO 29
<211> LENGTH: 9
<212> TYPE: PRT
<213> ORGANISM: Homo sapiens

<400> SEQUENCE: 29

Lys Thr Arg Arg Glu Ala Glu Asp Leu
1               5

<210> SEQ ID NO 30
<211> LENGTH: 9
<212> TYPE: PRT
<213> ORGANISM: Homo sapiens

<400> SEQUENCE: 30

Glu Asp Leu Gln Val Gly Gln Val Glu
1               5

<210> SEQ ID NO 31
<211> LENGTH: 25
<212> TYPE: PRT
<213> ORGANISM: Homo sapiens

<400> SEQUENCE: 31

Arg Glu Ala Glu Asp Leu Gln Val Gly Gln Val Glu Leu Gly Gly Gly
1               5                   10                  15

Pro Gly Ala Gly Ser Leu Gln Pro Leu
            20                  25

<210> SEQ ID NO 32
<211> LENGTH: 32
<212> TYPE: PRT
<213> ORGANISM: Homo sapiens

<400> SEQUENCE: 32

Arg Glu Ala Glu Asp Leu Gln Val Gly Gln Val Glu Leu Gly Gly Gly
1               5                   10                  15

Pro Gly Ala Gly Ser Leu Gln Pro Leu Ala Leu Glu Gly Ser Leu Gln
            20                  25                  30

<210> SEQ ID NO 33
<211> LENGTH: 10
<212> TYPE: PRT
<213> ORGANISM: Homo sapiens

<400> SEQUENCE: 33

Glu Ala Glu Asp Leu Gln Val Gly Gln Val
1               5                   10

<210> SEQ ID NO 34
```

```
<211> LENGTH: 11
<212> TYPE: PRT
<213> ORGANISM: Homo sapiens

<400> SEQUENCE: 34

Glu Ala Glu Asp Leu Gln Val Gly Gln Val Glu
1               5                   10

<210> SEQ ID NO 35
<211> LENGTH: 12
<212> TYPE: PRT
<213> ORGANISM: Homo sapiens

<400> SEQUENCE: 35

Glu Ala Glu Asp Leu Gln Val Gly Gln Val Glu Leu
1               5                   10

<210> SEQ ID NO 36
<211> LENGTH: 13
<212> TYPE: PRT
<213> ORGANISM: Homo sapiens

<400> SEQUENCE: 36

Glu Ala Glu Asp Leu Gln Val Gly Gln Val Glu Leu Gly
1               5                   10

<210> SEQ ID NO 37
<211> LENGTH: 14
<212> TYPE: PRT
<213> ORGANISM: Homo sapiens

<400> SEQUENCE: 37

Glu Ala Glu Asp Leu Gln Val Gly Gln Val Glu Leu Gly Gly
1               5                   10

<210> SEQ ID NO 38
<211> LENGTH: 20
<212> TYPE: PRT
<213> ORGANISM: Homo sapiens

<400> SEQUENCE: 38

Glu Ala Glu Asp Leu Gln Val Gly Gln Val Glu Leu Gly Gly Gly Pro
1               5                   10                  15

Gly Ala Gly Ser
            20

<210> SEQ ID NO 39
<211> LENGTH: 22
<212> TYPE: PRT
<213> ORGANISM: Homo sapiens

<400> SEQUENCE: 39

Glu Ala Glu Asp Leu Gln Val Gly Gln Val Glu Leu Gly Gly Gly Pro
1               5                   10                  15

Gly Ala Gly Ser Leu Gln
            20

<210> SEQ ID NO 40
<211> LENGTH: 23
<212> TYPE: PRT
<213> ORGANISM: Homo sapiens

<400> SEQUENCE: 40

Glu Ala Glu Asp Leu Gln Val Gly Gln Val Glu Leu Gly Gly Gly Pro
```

-continued

```
1               5               10              15

Gly Ala Gly Ser Leu Gln Pro
            20

<210> SEQ ID NO 41
<211> LENGTH: 24
<212> TYPE: PRT
<213> ORGANISM: Homo sapiens

<400> SEQUENCE: 41

Glu Ala Glu Asp Leu Gln Val Gly Gln Val Glu Leu Gly Gly Gly Pro
1               5               10              15

Gly Ala Gly Ser Leu Gln Pro Leu
            20

<210> SEQ ID NO 42
<211> LENGTH: 25
<212> TYPE: PRT
<213> ORGANISM: Homo sapiens

<400> SEQUENCE: 42

Glu Ala Glu Asp Leu Gln Val Gly Gln Val Glu Leu Gly Gly Gly Pro
1               5               10              15

Gly Ala Gly Ser Leu Gln Pro Leu Ala
            20              25

<210> SEQ ID NO 43
<211> LENGTH: 26
<212> TYPE: PRT
<213> ORGANISM: Homo sapiens

<400> SEQUENCE: 43

Glu Ala Glu Asp Leu Gln Val Gly Gln Val Glu Leu Gly Gly Gly Pro
1               5               10              15

Gly Ala Gly Ser Leu Gln Pro Leu Ala Leu
            20              25

<210> SEQ ID NO 44
<211> LENGTH: 27
<212> TYPE: PRT
<213> ORGANISM: Homo sapiens

<400> SEQUENCE: 44

Glu Ala Glu Asp Leu Gln Val Gly Gln Val Glu Leu Gly Gly Gly Pro
1               5               10              15

Gly Ala Gly Ser Leu Gln Pro Leu Ala Leu Glu
            20              25

<210> SEQ ID NO 45
<211> LENGTH: 28
<212> TYPE: PRT
<213> ORGANISM: Homo sapiens

<400> SEQUENCE: 45

Glu Ala Glu Asp Leu Gln Val Gly Gln Val Glu Leu Gly Gly Gly Pro
1               5               10              15

Gly Ala Gly Ser Leu Gln Pro Leu Ala Leu Glu Gly
            20              25

<210> SEQ ID NO 46
<211> LENGTH: 29
<212> TYPE: PRT
```

-continued

```
<213> ORGANISM: Homo sapiens

<400> SEQUENCE: 46

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser
            20                  25

<210> SEQ ID NO 47
<211> LENGTH: 30
<212> TYPE: PRT
<213> ORGANISM: Homo sapiens

<400> SEQUENCE: 47

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu
            20                  25                  30

<210> SEQ ID NO 48
<211> LENGTH: 31
<212> TYPE: PRT
<213> ORGANISM: Homo sapiens

<400> SEQUENCE: 48

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 49
<211> LENGTH: 18
<212> TYPE: PRT
<213> ORGANISM: Homo sapiens

<400> SEQUENCE: 49

Gly Ser Leu Gln Pro Leu Ala Leu Glu Gly Ser Leu Gln Lys Arg Gly
1               5                   10                  15

Ile Val
```

PROINSULIN PEPTIDES FOR TYPE 1 DIABETES

FIELD OF THE INVENTION

The invention relates to one or more peptides which can be used in the therapy or prevention of Type 1 Diabetes (T1D).

BACKGROUND TO THE INVENTION

Type 1 Diabetes (T1D) is an auto-immune disease characterised by metabolic dysfunction, most notably dysregulation of glucose metabolism, accompanied by characteristic long-term vascular and neurological complications. T1D is one of the most common autoimmune diseases, affecting one in 250 individuals in the US where there are approximately 10,000 to 15,000 new cases reported each year, and the incidence is rising. The highest prevalence of T1D is found in northern Europe.

T1D is characterised by absolute insulin deficiency, making patients dependent on exogenous insulin for survival. Prior to the acute clinical onset of T1D with symptoms of hyperglycaemia there is a long asymptomatic preclinical period, during which insulin-producing beta cells are progressively destroyed.

Once initiated, treatment with injections of synthetic insulin is required for life since beta cells do not re-generate. Once established, diabetes is a major burden to the patient, to the patient's family, and to society. Although modern dosages, preparations and delivery systems for insulin can maintain blood glucose within reasonable limits, over several years complications of the disease inevitably occur. The most common severe complications of diabetes are kidney failure, blindness, and loss of nerve function. The life span of a patient with diabetes is reduced by an average of 10 years. In light of this background, it is important to consider new means of treating or preventing T1D.

T1D like all autoimmune diseases, results from the inappropriate activation of the immune system in response to autoantigen encounter, specifically by short peptide sequences presented to it by specific HLA molecules. Although the condition can be managed increasingly well clinically, it still impacts negatively on quality of life and life expectancy.

The reasons for the loss of self-tolerance in type 1 diabetes remain debated, but it is well established that the HLA system constitutes a major genetic risk factor. HLA-DR3-DQ2 (DRB1*03:01-DQA1*05:01-DQB1*02:01) is the most common haplotype found in type 1 diabetes patients, at around 34% (Erlich H et al. (2008) Diabetes 57(4): 1084-1092) and thus delineates a major, identifiable disease cohort. Given the antigen-presenting properties of HLA molecules, it is assumed that the diabetes risk associated with HLA-DR3-DQ2 relates to the selective presentation of peptide epitopes of potentially diabetogenic autoantigens. Therefore, identification of these autoantigens and specific disease-determining regions is an important step towards understanding disease aetiology.

Attempts to discover disease-relevant epitopes in clinical studies generally involve the elution or prediction of peptides bound to candidate HLA molecules on antigen-presenting cells and/or in vitro examination of T cell responses in subjects with type 1 diabetes. This approach has generated several potentially relevant HLA-DR3-DQ2-restricted epitopes from a number of islet antigens, including Glutamic Acid Decarboxylase 65 (GAD65) and Islet Antigen-2 (IA-2)

(Di Lorenzo T P et al. (2007) Clin Exp Immunol 148(1): 1-16). Interestingly, proinsulin, generally considered to be involved in the early stages of type 1 diabetes in both humans and mice (Narendran P, et al. (2003) Autoimmun Rev 2(4): 204-210), has not been identified as a robust source of diabetes-related epitopes presented by HLA-DR3-DQ2. One recent study, however, has highlighted regions of proinsulin C-peptide as generating HLA-DQ2-restricted CD4$^+$ T cell responses in subjects with type 1 diabetes (So M et al. (2018) Proc Natl Acad Sci USA 115(42): 10732-10737).

Preclinical data in mouse models has often suggested that there are "driver T cells"—namely cohorts of T cells focused onto a single peptide region of the autoantigen. The importance of these is that they have a bigger impact on disease. As a therapeutic corollary of that, if driver T cells can be nullified, then the effect on controlling disease is better than using targets/T-cells that are second line; sub-dominant. The driver T cells and relevant peptides from antigens can be very hard to find in human disease. As the disease develops over time, many sub-dominant T cell clones and targets can become involved, masking the driver T cells/targets.

The present invention addresses how to identify the molecular targets of driver T cells with relevance to human type 1 diabetes. By identifying these peptides, peptide immunotherapy could incapacitate the most important disease drivers. This is particularly important and effective in individuals where autoimmunity has not been initiated.

The present inventors have utilised an in vivo approach to epitope discovery, using diabetes-susceptible, HLA-transgenic mice. The disease relevance of antigens and peptides was examined by their ability to promote the development of autoimmune diabetes in susceptible animals. The HLA-DR3-DQ2-transgenic mouse used in the art does not develop diabetes spontaneously (de Kauwe A L et al. (2009) J Immunol 182(12): 7440-7450). In order to promote this disease phenotype, the inventors generated a novel HLA-transgenic mouse model that expresses high risk genes for type 1 diabetes (DRB1*03:01-DQA1*05:01-DQB1*02:01) as well as human CD80 beta cell-specific expression of the costimulatory molecule CD80 (B7.1) under the Rat Insulin Promoter (RIP) and human CD4, on a C57BL/6 background. The application of adjuvanted antigen priming as a mechanism to accelerate and extend diabetes penetrance demonstrates the importance of specific islet antigens as a diabetogenic driver in the HLA-DR3-DQ2 background. The inventors have highlighted a novel, HLA-guided approach to identify disease-relevant antigenic drivers in vivo, and have identified novel, non-naturally, occurring peptides which could be used in peptide immunotherapy to induce tolerance. The inventors have pinpointed the diabetogenic effect of proinsulin to a previously unreported region that commences at the C-terminal end of the B-chain.

Peptides from the B23-C20 region of proinsulin of the present invention, murine or human, have not previously been identified as being either HLA-DR3 or HLA-DQ2-restricted. Furthermore, no previous study has directly demonstrated diabetogenicity of this region in association with any haplotype; indeed, the approach of using antigen-adjuvanted priming against selected HLA backgrounds to explore the potential diabetogenicity and relative primacy of antigens and epitopes has not been suggested.

Few studies have examined T cell reactivity to the B-C junction, and fewer still for HLA-DR3/DQ2 restricted responses. Semana et al previously found HLA-DR-restricted CD4$^+$ T cell responses to proinsulin peptide C3-16, in diabetes patients, but these were not analysed for HLA (Semana G, et al. (1999) J Autoimmun 12(4): 259-267). In autoantibody-positive individuals of the HLA-DRB1*0401/DQB1*0302 genotype (HLA-DR4/DQ8 haplotype), the long B11-C24 peptide is recognised frequently (Durinovic-Bello I, et al. (2002) J Autoimmun 18(1): 55-66). So et al. identified CD4⁺ T cell responses to C2-11 and C3-14 in 3 out of their 22 T cell clones, but with HLA-DQ8 restriction (So M, et al. (2018) Proc Natl Acad Sci USA 115(42): 10732-10737.). HLA-DQ2-restricted peptides able to generate a T cell response were all located near the C-terminal end of C-peptide. Rudy et al. (Rudy G, et al. (1995) Mol Med 1:625-633) examined T cell responses to a single proinsulin peptide B24-C4 in subjects without diabetes but at high risk of developing the disease due to the presence of autoantibodies. T cell responses were present in 6/10 subjects. Subjects were HLA-DR3 or -DR4 or heterozygous for these and responses were not linked to any specific haplotype. Raju et al. (Raju R et al. (1997) Hum Immunol 58:21-29) examined T cell responses to each of 10 overlapping peptides of proinsulin in mice transgenic for HLA-DQ8 after immunization with the same peptide. DQ8-restricted responses were seen to B1-B24 and B20-C10 in DQ8 mice. These mice do not have diabetes and this study does not provide any disease insights.

None of the available prior art discloses the presently claimed peptides which have significant therapeutic potential, particularly in the DR3-DQ2 haplotype.

SUMMARY OF THE INVENTION

In a first aspect of the invention, there is provided a peptide having at least 78% homology to the amino acid sequence of SEQ ID NO: 1; SEQ ID NO: 2; SEQ ID NO: 3; SEQ ID NO: 4 or SEQ ID NO: 5.

SEQ ID NO: 1 is a fragment of PI, comprising residues B30-C13.

SEQ ID NO: 2 is a fragment of PI, comprising residues B29-C11.

SEQ ID NO: 3 is a fragment of PI, comprising residues C1-C14.

SEQ ID NO: 4 is a fragment of PI, comprising residues B29-C14.

SEQ ID NO: 5 is a fragment of PI, comprising residues B23-C20.

The present inventors have surprisingly found that these novel, non-naturally occurring peptides could be used in peptide immunotherapy to induce tolerance. The inventors have pinpointed the diabetogenic effect of proinsulin to this previously unreported region that commences at the C-terminal end of the B-chain.

The peptides are non-naturally occurring due to the presence of at least one R from the R:R motif which is naturally cleaved by PC1/3 (proprotein convertase 1, also known as prohormone convertase; and prohormone convertase 3, or neuroendocrine convertase 1 and often abbreviated as PC1/3) which cleaves the R:R motif between the B and C chains as part of the normal processing of the prohormone proinsulin into insulin and C-peptide.

Theses peptides have not previously been identified as being either HLA-DR3 or HLA-DQ2-restricted.

As herein described the term "peptide" refers to any peptide comprising amino acids joined to each other by peptide bonds or modified peptide bonds, i.e., peptide isosteres. The peptide generally will contain naturally occurring amino acids but may include amino acid sequences modified either by natural processes, such as post-translational processing, or by chemical modification techniques which are well known in the art. Such modifications are well described in basic texts. Modifications can occur anywhere in a peptide, including the peptide backbone, the amino acid side-chains and the amino or carboxyl termini. It will be appreciated that the same type of modification may be present in the same or varying degrees at several sites in a given peptide. Also, a given peptide may contain many types of modifications.

The peptide has at least 78% homology to the amino acid sequence of SEQ ID NO: 1; SEQ ID NO: 2; SEQ ID NO: 3; SEQ ID NO: 4 or SEQ ID NO: 5. In some embodiments, the peptide has at least 80% homology to the amino acid sequence of SEQ ID NO: 1; SEQ ID NO: 2; SEQ ID NO: 3; SEQ ID NO: 4 or SEQ ID NO: 5. In some embodiments, the peptide has at least 85% homology to the amino acid sequence of SEQ ID NO: 1; SEQ ID NO: 2; SEQ ID NO: 3; SEQ ID NO: 4 or SEQ ID NO: 5. In some embodiments, the peptide has at least 90% homology to the amino acid sequence of SEQ ID NO: 1; SEQ ID NO: 2; SEQ ID NO: 3; SEQ ID NO: 4 or SEQ ID NO: 5. In some embodiments, the peptide has at least 95% homology to the amino acid sequence of SEQ ID NO: 1; SEQ ID NO: 2; SEQ ID NO: 3; SEQ ID NO: 4 or SEQ ID NO: 5. In some embodiments, the peptide has at least 99% homology to the amino acid sequence of SEQ ID NO: 1; SEQ ID NO: 2; SEQ ID NO: 3; SEQ ID NO: 4 or SEQ ID NO: 5. In a particular embodiment, the peptide has the amino acid sequence of SEQ ID NO: 1; SEQ ID NO: 2; SEQ ID NO: 3; SEQ ID NO: 4 or SEQ ID NO: 5. In a further embodiment, the peptide has the amino acid sequence of SEQ ID NO: 1 or SEQ ID NO: 2.

Where the amino acid does not have the amino acid sequence of SEQ ID NO: 1; SEQ ID NO: 2; SEQ ID NO: 3; SEQ ID NO: 4 or SEQ ID NO: 5 it is preferable that the amino acid changes are conservative, i.e. the amino acid is changed to a different amino acid with similar biochemical properties (e.g. charge, hydrophobicity and size).

Preferably, the peptides which make up the peptide combination are isolated peptides. The term "isolated" means that the peptide is removed from its original environment. For example, a peptide present in a living animal is not isolated, but the same peptide, or a fragment of such a peptide, separated from some or all of the coexisting materials in the natural system, is isolated. Such peptides could be part of a vector and/or peptides could be part of a composition, and still be isolated in that such vector or composition is not part of its natural environment.

In a preferred embodiment, there is provided a peptide combination comprising two or more of the peptides described above.

A second aspect of the invention relates to a pharmaceutically acceptable composition comprising the peptide or peptide combination of the present invention and one or more pharmaceutically acceptable excipients.

Preferably the pharmaceutical composition comprising cysteine. The presence of free cysteine within the composition stabilises any tendency for the peptides of present invention to form inter-chain disulphide bonds and thus precipitate. The pharmaceutical composition may comprise 1 to 5 mg of L-cysteine per 2 mg of peptide, preferably 2 to 4 mg of L-cysteine per 2 mg of peptide and most preferably, 2.5 mg of L-cysteine per 2 mg of peptide.

The pharmaceutical composition may be for human or animal usage in human and veterinary medicine and will typically comprise one or more suitable excipients. Acceptable excipients for therapeutic use are well known in the pharmaceutical art, and are described, for example, in Remington's Pharmaceutical Sciences, Mack Publishing Co. (A. R. Gennaro edit. 1985). The choice of pharmaceutical excipient can be selected with regard to the intended route of administration and standard pharmaceutical practice. The pharmaceutical compositions may comprise as, or in addition to, the excipient any suitable binder, lubricant, suspending agent, coating agent or solubilising agent.

Preservatives, stabilizers and dyes may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered parenterally in which the composition is formulated in an injectable form, for delivery, by, for example, an intravenous, intradermal, intramuscular, subcutaneous or intraperitoneal route. For parenteral administration, the compositions may be best used in the form of a sterile aqueous solution which may contain other substances, for example enough salts or monosaccharides to make the solution isotonic with blood. The composition may also be formulated to be administered by oral or topical routes, including nasally, orally or epicutaneously. Preferably the composition is formulated to be delivered by an intradermal route.

Intradermal administration routes include any dermal-access means, for example, using microneedle-based injection and infusion systems (or other means to accurately target the intradermal space), needleless or needle-free ballistic injection of fluids or powders into the intradermal space, Mantoux-type intradermal injection, enhanced iontophoresis through microdevices, and direct deposition of fluid, solids, or other dosing forms into the skin, including the use of patches to deposit the composition onto the skin.

Typically, a physician will determine the actual dosage which will be most suitable for an individual subject and it will vary with the disease, age, weight and response of the particular patient. The appropriate dosage for humans can be determined by one skilled in the art, for example using body surface area (BSA) normalisation. For example, the pharmaceutical composition may comprise about 0.1 μg to 15 mg total peptide per single dose, preferably 1 μg to 12 mg total peptide per single dose. In one preferred embodiment, 240 μg (1 μg dose BSA normalized for a 60 kg adult human) of total peptide per single dose is administered. In another preferred embodiment, 12 mg of total peptide per single dose is administered. If more than one peptide is administered, preferably the peptides are present in an equimolar ratio.

In a preferred embodiment, the pharmaceutical composition of the present invention is administered at least once per month, preferably at least once per month for up to twelve administrations.

The pharmaceutical composition may also comprise tolerance-promoting adjuvants and/or tolerance promoting cells. Tolerance promoting adjuvants include IL-10, recombinant cholera toxin B-subunit (rCTB), ligands for Toll-like receptor 2, as well as biologics and monoclonal antibodies that modulate immune responses, such as anti-CD3, co-stimulation blockers and immune checkpoint modulators, which may be co-administered with the peptide combination. Tolerance promoting cells include regulatory T cells, immature dendritic cells and dendritic cells treated with vitamin D3, (1alpha,25-dihydroxy vitamin D3) or its analogues. Preferably one or more of the peptides of the present invention are conjugated to the surface of a dendritic cell treated with vitamin D3 or its analogues.

The peptide or peptide combination of the present invention may be coated on a nanoparticle within the pharmaceutical acceptable composition. The nanoparticle may be a carbon-based nanoparticle, ceramic nanoparticle, metal nanoparticle, semiconductor nanoparticle, polymeric nanoparticle or lipid-based nanoparticles or mixture thereof.

In one embodiment the peptide or peptide combination is coated on the nanoparticle by means of being bound to an MHC complex which is attached to the nanoparticle.

A third aspect of the invention relates to the pharmaceutically acceptable composition of the present invention for use in therapy.

A fourth aspect of the invention relates to the pharmaceutically acceptable composition of the present invention for use in the treatment or prevention of Type 1 Diabetes (T1D).

When T1D is "treated", this means that one or more clinical manifestations of T1D are ameliorated. It does not mean that the symptoms of T1D are completely remedied so that they are no longer present in the patient, although in some methods, this may be the case. "Treatment" results in one or more of the symptoms of T1D being less severe than before treatment.

Preferably, the pharmaceutical composition of the present invention is for use in the treatment or prevention of (T1D) wherein the patient has a DR3 haplotype. Preferably the patient has a DR3-DQ2 haplotype. The inventors have surprisingly and specifically demonstrated the importance of the presently claimed peptides as diabetogenic drivers on the HLA-DR3-DQ2 background.

A fifth aspect of the invention relates to the pharmaceutically acceptable composition of the present invention for use in the manufacture of a medicament for the treatment or prevention of Type 1 Diabetes (T1D).

A sixth aspect of the invention relates to a method of treatment or prevention of Type 1 Diabetes (T1D) in which the pharmaceutically acceptable composition of the present invention is administered to a patient with T1D or a non-diabetic individual identified as being at high-risk of T1D.

Preferably the pharmaceutically acceptable composition of the present invention is administered to a patient who has beta cell mass remaining.

A seventh aspect of the invention relates to a kit for the treatment or prevention of Type 1 Diabetes (T1D) which comprises the peptide or peptide combination of the present invention.

An eighth aspect of the invention relates to a nucleotide sequence encoding the peptide of the present invention.

A ninth aspect of the invention relates to a vector expressing any one of the peptides of the present invention.

The vector may be any appropriate vector for expressing the peptides of the present invention, including viral and non-viral vectors. Viral vectors include a parvovirus, an adenovirus, a retrovirus, a lentivirus or a herpes simplex virus. The parvovirus may be an adenovirus-associated virus (AAV). The vector is preferably a recombinant adeno-associated viral (rAAV) vector or a lentiviral vector. More preferably, the vector is a rAAV vector.

A vector according to the invention may be a gene delivery vector. Such a gene delivery vector may be a viral gene delivery vector or a non-viral gene delivery vector.

Accordingly, the present invention provides gene delivery vectors based on animal parvoviruses, in particular dependoviruses such as infectious human or simian AAV, and the components thereof (e.g., an animal parvovirus genome) for use as vectors for introduction and/or expression of the peptides of the present invention in a mammalian cell. The term "parvoviral" as used herein thus encompasses dependoviruses such as any type of AAV.

A tenth aspect of the present invention relates to a genetically modified animal which spontaneously develops T1D, wherein the animal has a DR3 haplotype, preferably a DR3-DQ2 haplotype. Preferably the animal is a non-human mammal, especially a primate. Alternatively, the animal may be a rodent, especially a mouse; or may be canine, feline, ovine or porcine. Preferably the animal comprises cells which express human CD80 under the Rat Insulin Promoter (RIP).

An eleventh aspect of the invention relates to a method for identifying T1D-relevant antigen drivers comprising priming the animal described above with peptides from the B23-C20 region of proinsulin and identifying a peptide as an antigen driver if disease progression was accelerated.

In one embodiment, disease progression is considered to be accelerated if it progresses 50% faster than if priming did not take place. Preferably the peptides are selected from those having at least 78% homology to the amino acid sequence of SEQ ID NO: 1; SEQ ID NO: 2; SEQ ID NO: 3; SEQ ID NO: 4 or SEQ ID NO: 5. In one embodiment, the peptides are administered in combination with an adjuvant as disclosed above. The peptides may be administered at a dosage of up to 1 mg per peptide.

A twelfth aspect of the invention relates to a method of diagnosis or determining treatment efficacy comprising: (a) providing CD4 lymphocytes from an individual suspected of having or being susceptible to T1D; (b) providing a population of Antigen Presenting Cells (APCs) which bear on their surface a class II MHC molecule of an allele identical to one expressed by said individual, the population of APCs having been contacted with the peptide or peptide combination of the present invention and the class II MHC molecule being bound to one or more of the peptides of the present invention; or (c) providing a soluble peptide-HLA multimer reagent comprising class II MHC molecules of an allele identical to one expressed by said individual, the MHC molecules having been bound to one or more peptides of the peptide combination of the present invention; (d) contacting the population of APCs of (b) or the peptide-HLA multimer of (c) with the CD4 lymphocytes of (a); and (e) determining whether the CD4 lymphocytes recognize the class II MHC-bound peptide, as an indication that the individual has, or is, susceptible to T1D.

Such APC can be B-lymphocytes, monocytes, macrophages, or dendritic cells, or whole peripheral blood mononuclear cells (PBMC). APC can also be immortalised cell lines derived from B-lymphocytes, monocytes, macrophages, or dendritic cells. Where the subjects are humans, the APC can also be T cells since human T cells are capable of expressing class II MHC molecules. The method further comprises administering the peptide or peptide combination of the present invention to the individual if the CD4 lymphocytes recognise the class II MHC-bound peptide.

Thirteenth and fourteenth aspects of the invention relate to methods of identifying a subject as being at high-risk of T1D and identifying a patient as being suitable for T1D treatment respectively, the methods comprising: determining whether the subject or patient has a DR3 haplotype, preferably a DR3-DQ2 haplotype, when an immune response to any one of the peptides or peptide combination of the invention is detected.

One skilled in the art would be familiar with ways to measure the immune response by CD4 T cells to the peptides of the invention. Examples include enzyme-linked immunospot assays (ELISPOT), peptide-HLA tetramer assays, or in vitro stimulation assays followed by detection of proliferating or cytokine-producing CD4 T cells.

A fifteenth aspect of the invention relates to methods of identifying a subject as being either a responder to immunotherapy or as requiring re-treatment with the peptides or peptide combination of the present invention, the method comprising: determining whether an immune response to any one of the peptides or peptide combination of the invention is detected.

Again the immune response can be detected for example, by ELISPOT, peptide-HLA tetramer assays, or in vitro stimulation assays followed by detection of proliferating or cytokine-producing CD4 T cells. If there is no immune response, or indeed the subject's immune response decreases, then the subject is responding to the immunotherapy. If the subject's immune response increases, then they may need further treatment with the peptides or the peptide combination of the invention.

A skilled person will appreciate that all aspects of the invention, whether they relate to, for example, the peptide, the peptide combination, its use, the pharmaceutically acceptable composition or a method of treatment are equally applicable to all other aspects of the invention. In particular, aspects of the peptide for example, may have been described in greater detail than in other aspects of the invention, for example, the use of the peptide. However, the skilled person will appreciate where more detailed information has been given for a particular aspect of the invention, this information is generally equally applicable to other aspects of the invention.

DETAILED DESCRIPTION OF THE INVENTION

The invention will now be described in detail by way of example only with reference to the figures in which:

FIG. 1 shows that DR3DQ2xRIP-B7.1 mice develop immune-mediated diabetes spontaneously.
- (a) 32 males and 24 females were monitored weekly for diabetes from the age of 6-7 weeks until the age of 35 weeks. Statistical analysis with Mantel-Cox Log-rank test. n.s.=not significant.
- (b) Representative images of immunohistochemical double staining of frozen pancreas section from a mouse with confirmed diabetes. Insulin stained in red, immune cells in brown. 20× Objective. Arrows indicate Ly6G$^+$ cells.
- (c-d) IgG autoantibody ELISAs for anti-human GAD65 protein (c) and anti-mouse proinsulin-2 overlapping 30-mer peptides (d). c+d: Analysis of sera obtained cross-sectionally from mice aged 8-23 weeks. Horizontal lines indicate median. Dunnett's multiple comparisons test. 10-22 samples per age bracket. ELISAs performed on the same samples, in parallel. * p<0.05, *** p<0.001.

Figure 2:
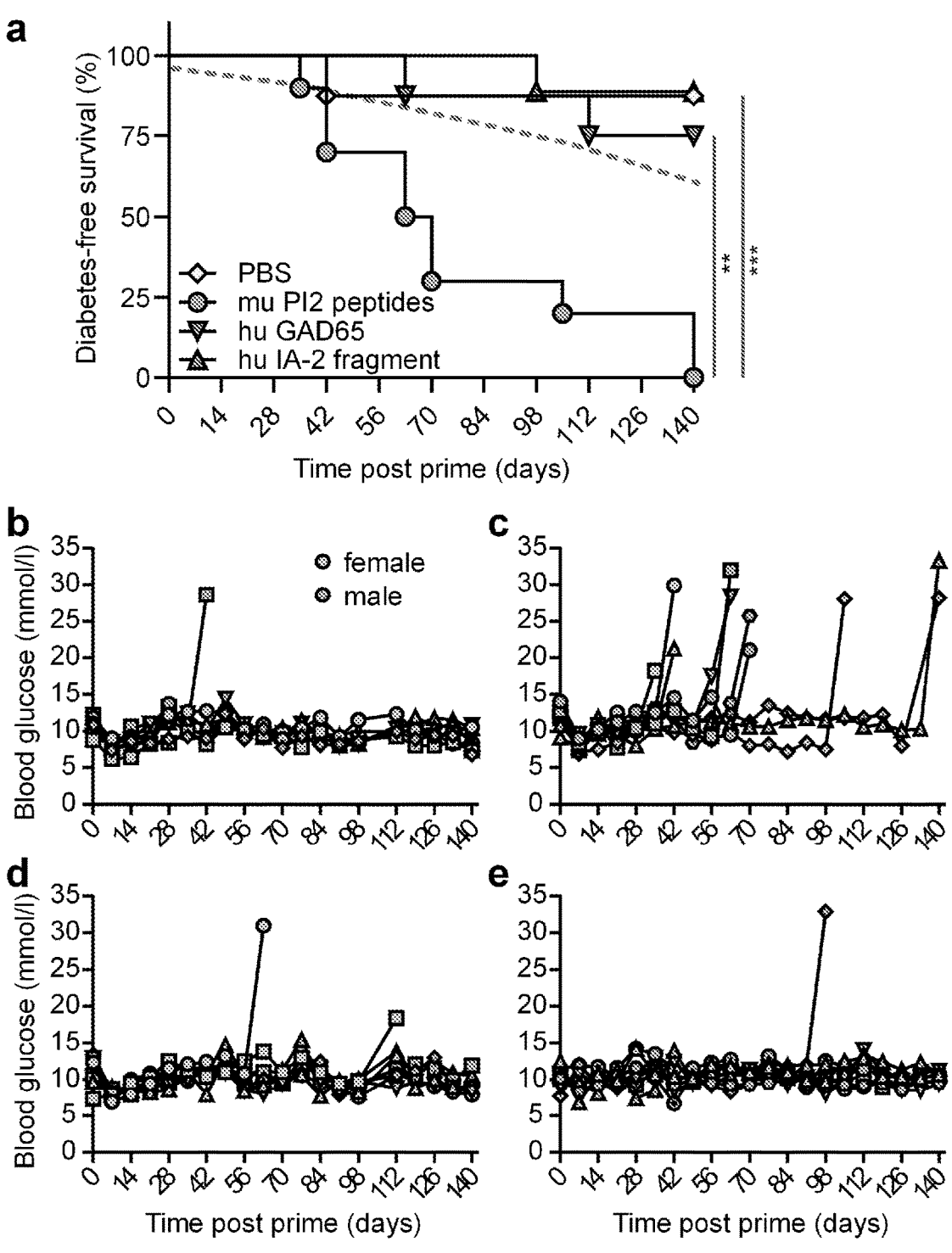

FIG. 2 shows adjuvanted priming with murine proinsulin-2 peptides promotes diabetes.
- (a) DR3DQ2xRIP-B7.1 mice aged 7-12 weeks were challenged with 100 µg of either murine proinsulin-2 peptides (6 ♂ 4 ♀), human GAD65 protein (5 ♂ 3 ♀) or the 377-aa C-terminal region of IA-2 (7 ♂ 2 ♀), and a PBS only control (5 ♂ 3 ♀) in TiterMax Gold adjuvant s.c. on days 0 and 14, with 200 ng pertussis toxin administered i.p on days 0 and 1 or 2. Mice were monitored weekly for diabetes up to 20 weeks post prime. The grey dotted line indicates the expected level of spontaneous diabetes in mice aged 12 weeks on day 0 of the experiments (based on the data in FIG. 1 and normalised for gender). Statistical analysis with Mantel-Cox Log-rank test.  p<0.01, * p<0.001.

(b-e) Blood glucose levels for each individual mouse in the group immunised with PBS (b), murine proinsulin-2 peptides (c), human GAD65 (d) or fragment of human IA-2 (e).

Figure 3:
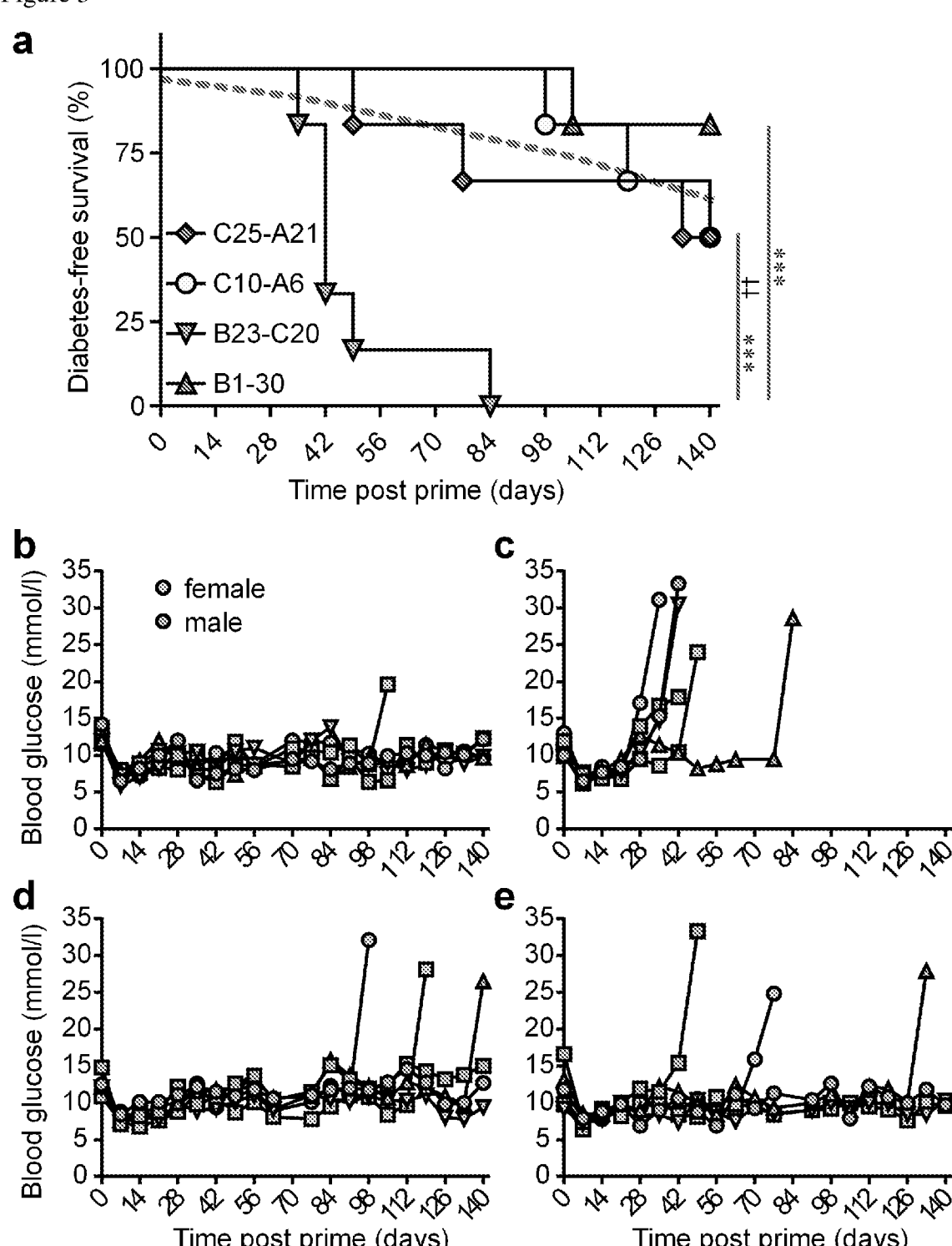

FIG. 3 shows that murine proinsulin-2 peptide B23-C20 mediates diabetogenicity.

(a) DR3DQ2xRIP-B7.1 mice aged 7-8 weeks (3 ♂ 3 ♀ in each group) were challenged with 100 μg of either murine 30-mer proinsulin-2 peptide B1-30, B23-C20, C10-A6, or C25-A21 in TiterMax Gold adjuvant s.c. on days 0 and 14, with 200 ng pertussis toxin administered i.p on days 0 and 1 or 2. Mice were monitored weekly for diabetes up to 20 weeks post prime. The grey dotted line indicates the expected level of spontaneous diabetes in mice aged 8 weeks on day 0 of the experiment, based on the data in FIG. 1 and normalised for gender. Statistical analysis with Mantel-Cox Log-rank test. *** p<0.001 for B23-C20 versus B1-30 or C10-A6. †† p<0.01 for B23-C20 versus C25-A21. Rest not significant.

(b-e) Blood glucose levels for each individual mouse in the group immunised with B1-30 (b), B23-C20 (c), C10-A6 (d) or C25-A21 (e).

FIG. 4 shows analysis and comparison of proinsulin-2 B23-C20.

(a) top: alignment of murine proinsulin-2 with the equivalent region of human proinsulin. Boxed amino acids are identical, shaded are similar. Below: 6 overlapping 14-15-mer murine peptides generated for more detailed analysis.

(b) Binding predictions for HLA-DR3 and HLA-DQ2 of all 6 murine peptides. For VD-14 peptide the preceding glutamine (Q) in the sequence was added for the prediction, to reach the minimum 15 amino acid length required. Predicted HLA binding cores and affinities were generated with the online IEDB analysis resource (tools.immuneepitope.org/mhcii/), using the NetMHCIIpan prediction method.

(c) Binding predictions for HLA-DR3 and HLA-DQ2 of human equivalents of the murine peptides. Predicted HLA binding cores and affinities were generated with the online IEDB analysis resource (tools.immuneepitope.org/mhcii/), using the NetMHCIIpan prediction method.

FIG. 5 shows that the ME-15 peptide (B29-C11) covers the core region of B23-C20 for diabetogenicity. (a) DR3DQ2xRIP-B7.1 mice aged 10-14 weeks were challenged with 100 μg of either GP-15 (2 ♂ 3 ♀), YA-15 (2 ♂ 3 ♀), ME-15 (3 ♂ 2 ♀), RG-15 (3 ♂ 2 ♀), DA-15 (2 ♂ 3 ♀) or VD-14 (3 ♂ 2 ♀) peptide in TiterMax Gold adjuvant s.c. on days 0 and 14, with 200 ng pertussis toxin administered i.p on days 0 and 1 or 2. Mice were monitored weekly for diabetes up to 20 weeks post prime. The grey dotted line indicates the expected level of spontaneous diabetes in mice aged 14 weeks on day 0 of the experiments (based on the data in FIG. 1 and normalised for gender). Statistical analysis with Mantel-Cox Log-rank test. * p<0.05 for RG-15 versus YA-15, ** p<0.01 for ME-15 versus GP-15, YA-15 or VD-14. † p<0.05 for ME-15 versus DA-15. Rest not significant. (b-f) Blood glucose levels for each individual mouse in the group immunised with GP-15 (b), YA-15 (c), ME-15 (d), RG-15 (e), DA-15 (f), VD-14 (g).

FIG. 6 Tolerance induction against accelerated diabetes in RIP.CD80xDR3DQ2 mice. (a) Schedule of dosing. Mice aged 7-8 weeks (n=7 per group) were treated with soluble 14/15-mer peptide in PBS subcutaneously (s.c.) before and after acceleration of diabetes development by antigenic priming with 30-mer murine proinsulin-2 peptide B23-C20 in TiterMax Gold adjuvant on days 0 and 14. Pertussis toxin administered intraperitoneally (i.p.) on days 0 and 2. (b) Diabetes incidence in mice treated with 14/15-mer peptide ME-15 (1 ♀ 6 ♂), YA-15 (4 ♀ 3 ♂) or VD-14 (3 ♀ 4 ♂). Statistical analysis with Mantel-Cox Log-rank test. ME-15 versus YA-15, p<0.01; ME versus VD-14, p<0.05.

Figure 7:
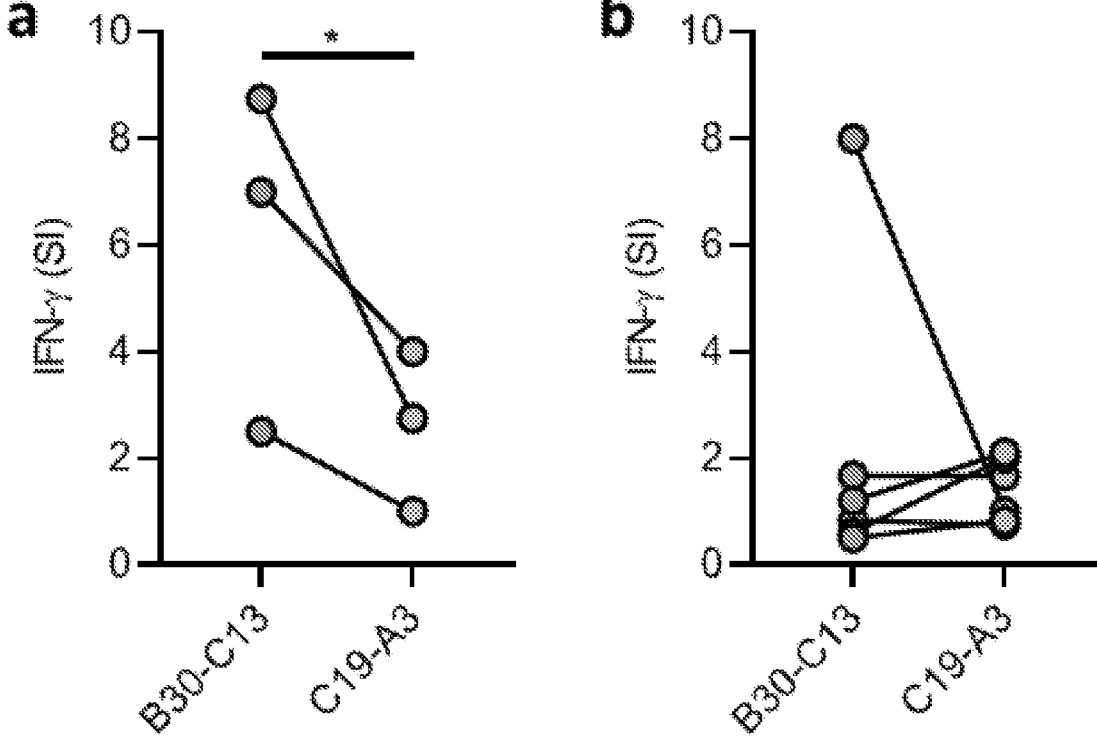

FIG. 7 shows antigen-specific responses in human donors detected by enzyme-linked immunospot (ELISPOT) assay.

Responses to proinsulin B30-C13 in human donors. PBMC from individuals with either HLA-DR3-DQ2 (a) or any other haplotype (b) were stimulated in vitro with human proinsulin-derived peptide B30-C13 or C19-A3 prior to detection of IFNγ by ELISPOT assay. HLA-DR3-DQ2 individuals, n=3; non-HLA-DR3-DQ2, n=6. * p<0.05, ratio paired t test.

Figure 8A:
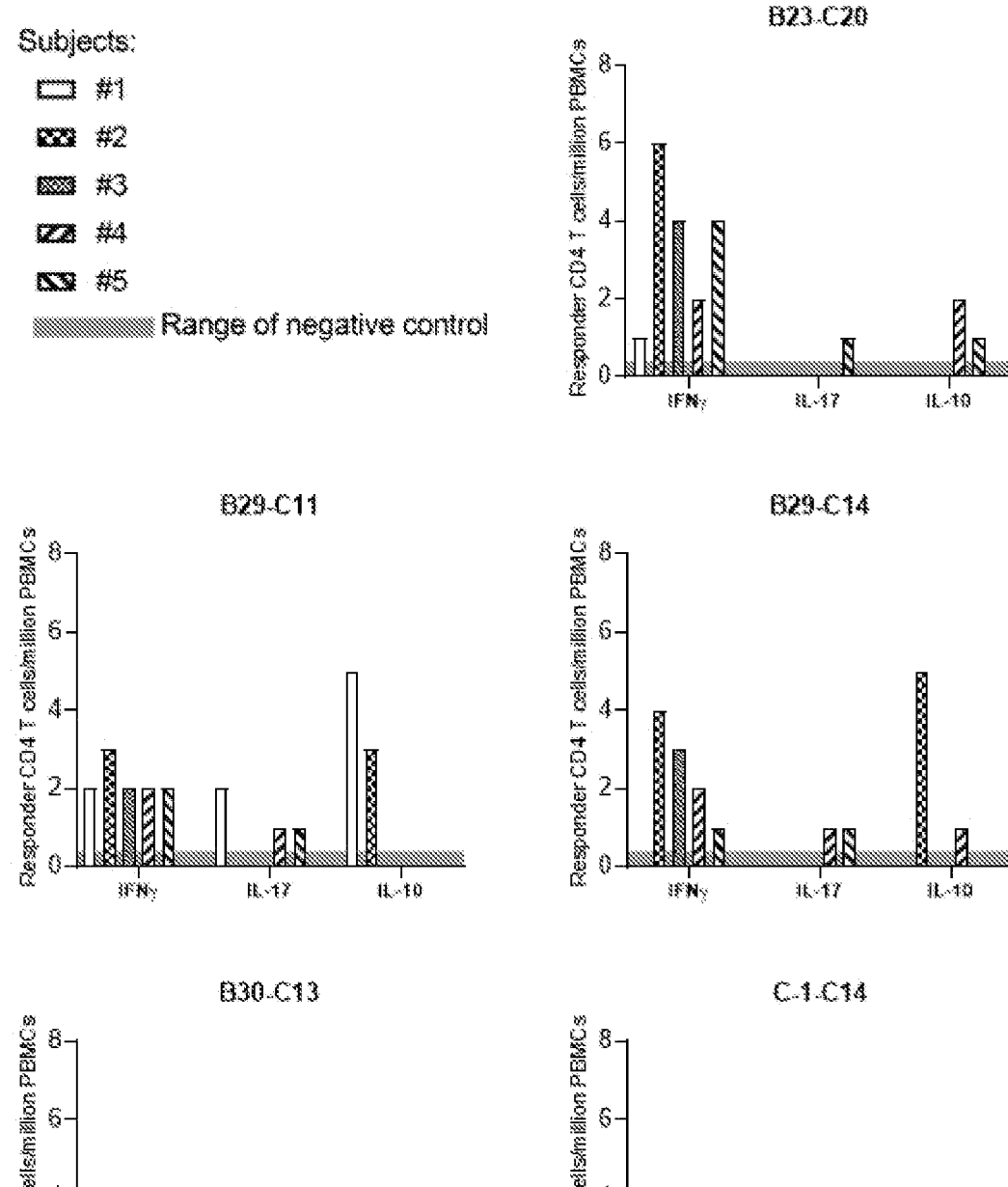

FIG. 8 shows antigen-specific responses in human donors with a recent diagnosis of type 1 diabetes and possessing HLA-DRB1*03:01-DQA1*05:01-DQB1*02:01 genotype (HLA-DR3/DQ2) detected by enzyme-linked immunospot (ELISPOT) assay.

Responses to proinsulin B23-C20, B29-C11, B29-C14, B30-C13 and $C_{-1}$-C14 peptides are shown. PBMCs from 5 type 1 diabetes patients with HLA-DR3-DQ2 (identified as #1-#5) were stimulated in vitro with human proinsulin-derived peptides B23-C20, B29-C11, B29-C14, B30-C13 and $C_{-1}$-C14 prior to detection of IFN-γ and IL-17 (pro-inflammatory responses) and IL-10 (regulatory response) by ELISPOT assay. (a) Data shown as raw counts of responder CD4 T cells per million PBMCs assayed for each peptide. Grey shading shows the upper limit of the negative control for each cytokine assay (mean 0.4, 0.2 and 0.2 CD4 T cells responding to diluent control for IFN-γ, IL-17 and IL-10 assays, respectively. (b) Summary tables showing positive responses (shaded boxes) for each patient/peptide.

EXAMPLE 1

Materials and Methods
Animals

HLA-DR3-DQ2-transgenic (B6.hCD4.DR3-DQ2. MHCII$^{-/-}$ mice (described previously (de Kauwe A L et al. (2009) J Immunol 182(12): 7440-7450), and obtained from J. McCluskey) were crossed with RIP-B7.1-transgenic animals (B6.Cg-Tg(Ins2-CD80)3B7Flv/Orl, EMMA, Orleans, France; ID 00216) in order to obtain HLA-DR3-DQ2$^+$ huCD4$^+$IA/IE$^{-/-}$RIP.B7.1$^+$ mice, hereafter referred to as DR3DQ2xRIP-B7.1. DR4xRIP-B7.1 mice, generated by crossing B6.129S2-H2-Ab1$^{tm1Gru}$ Tg(HLA-DRA/H2-Ea, HLA-DRB1*0401/H2-Eb)1Kito mice with B6.Cg-Tg(Ins2-CD80)3B7Flv/Orl, were described previously (Verhagen J, et al. (2018) Sci Rep 8(1): 14106). All animals were kept under specific-pathogen-free conditions, in individually ventilated cages, at the KCL Biological Services Unit on 12-hour light/dark cycles with food and water provided ad libitum. Experiments were conducted in accordance with UK Home Office regulations under a project license held by M. Peakman. All work was subject to assessment and approved locally by Guy's animal welfare and ethical review board (AWERB).

Priming Antigens

All murine proinsulin-2 peptides were custom manufactured by either Almac (Edinburgh, UK) or GLS Biochem (Shanghai, China) at >95% purity. The 377-amino acid c-terminal fragment of human IA-2 was produced by ProteoGenix (Schiltigheim, France). Recombinant human GAD65 (T-cell GAD) was purchased from Diamyd Medical (Stockholm, Sweden). Predicted HLA binding cores and affinities were generated with the online IEDB analysis resource (tools.immuneepitope.org/mhcii/), using the NetMHCIIpan prediction method.

Induction and Monitoring of Diabetes

All mice were monitored regularly for unprovoked glycosuria using Diastix strips (Bayer, Basel, Switzerland). Some mice were monitored weekly for hyperglycaemia, from the age of 6-7 weeks, by a minimal puncture of the tail vein at alternate sides of the tail and analysis using a OneTouch Verio meter and strips (Lifescan, High Wycombe, UK), in order to closely monitor progression towards spontaneous diabetes. Mice were considered diabetic following a blood glucose reading>16.7 mmol/1 (300 mg/dl) in addition to confirmed glycosuria. For disease acceleration experiments, animals were distributed over equal or similar sized groups as indicated to achieve a comparable spread of age and gender for each group. Mice (aged 6-14 weeks) were primed with 100 μg of peptides or protein in TiterMax Gold adjuvant (TiterMax, Norcross, GA, USA) subcutaneously (s.c.) at the base of the tail and received a second dose s.c. distributed over the inguinal region on day 14. Mice received 200 ng Pertussis toxin (Sigma, Poole, UK) in PBS intraperitoneally (i.p.) on days 0 and 1 or 2. Mice were then monitored weekly for hyperglycaemia and for glycosuria. In experiments to examine tolerance induction, mice received subcutaneous injections of 10 μg peptide in aqueous solution separate by 3-4 days for a total of 6 injections. Tolerance regimes commenced one week before adjuvanted antigen priming. Immediately upon detection of diabetes, mice were sacrificed humanely, according to ethical approval.

Histology

Pancreata embedded in OCT compound (Cellpath, Newtown, UK) were frozen in isopentane (Sigma) cooled with liquid nitrogen. 10 μm sections were fixed in acetone before first staining with rabbit anti-mouse insulin (Abcam), detected with Vector Impress anti-rabbit AP (Vector Labs, Peterborough, UK), and developed with Vector ImmPress Red. Immune cells in the tissues were stained with biotinylated antibodies to murine CD4 (clone GK1.5, also recognises human CD4), CD8, CD11b, CD11c, Ly6G and B220 (all from eBioscience/ThermoFisher, Altrincham, UK), which were detected using ABC reagent and DAB solution from Vector Labs. Nuclei were stained with hematoxylin (Sigma), before mounting slides with VectaMount (Vector Labs). Images were acquired on a Zeiss Axiovert A1 microscope using Zen software. No cropping or alteration of the images was used.

Autoantibody ELISA

Proinsulin-2 peptides or recombinant human GAD65 were coated onto Maxisorp plates (Nunc, Roskilde, Denmark) in ELISA coating buffer (eBioscience). Diluted sera (in PBS 5% BSA, Sigma) or controls (mouse IgG2a anti-insulin clone ICBTACLS and isotype from ThermoFisher, mouse IgG1 anti-GAD65 clone N-GAD65 and isotype from Biolegend) were incubated for 2 hours at room temperature prior to detection with biotin-anti-mouse IgG, Streptavidin-HRP and high sensitivity TMB solution (all from eBioscience) and read at 450 nm. Titrated concentrations (1-1000 ng/ml) of the relevant control antibody on each plate were used to normalise data and assign an arbitrary unit to serum antibody levels.

Analysis of C-Peptide Fragments Released by Human Beta Cells

To examine the full potential of C-peptide fragments to be available in vivo, we analysed (i) secretion into the supernatant by islet cells and (ii) secretion into intracellular granules.

(i) Secretion

Human pancreatic islets were washed in 1×DPBS containing 0.5 mM EDTA and preconditioned in Krebs-Ringer Buffer containing 2.5 mM glucose for 30 min at 37° C. at 5% $CO_2$. Buffer was then exchanged to Krebs-Ringer Buffer containing either 2.5 mM or 25 mM Glucose and islets were incubated for 30 min at 37° C. at 5% $CO_2$. Secretions in the supernatants under each condition were collected and centrifuged at 400×g for 5 min at 4° C. to pellet any residual cells. Secretion supernatants were collected and protein/fragments isolated and purified by C18 reverse-phase resin purification.

(ii) Intracellular Granules

Islets were washed three times in 1×DPBS containing 0.5 mM EDTA at 300×g for 3 min at room temperature. Islet cells were taken up in Accutase (prewarmed to 37° C.) at a concentration of 0.5 ml/1,000 IEQ (islet equivalent) and incubated for 10 min in a water bath at 37° C. The tube was inverted every minute and in addition after 5 and 10 min pipetted up and down five times with a 5 ml serological pipette to yield a single cell suspension. Suspensions were filtered through a 35 μm nylon mesh and washed in 1×DPBS 0.5 mM EDTA at 300×g for 3 min. Cells were resuspended in 2 ml 1×DBPS 0.5 mM EDTA. Cell membranes were disrupted while keeping intracellular compartments intact using a Balch homogeniser (Isobiotech, Germany) with a 14 μm pore size. Single cell lysates were passed through the homogeniser 10 times. Homogenised cells were centrifuged at 1,000×g for 15 min at 4° C. to release intracellular contents which were collected. The pellet was resuspended in 1×DPBS 0.5 mM EDTA and centrifuged again. Intracellular contents in the supernatant were collected again and pooled before centrifugation at 5,000×g for 15 min at 4° C. to yield a pellet containing high density intracellular compartments enriched for crinosomes. The supernatant from this spin was centrifuged again at 20,000×g for 45 min at 4° C. to yield a pellet low density intracellular compartments enriched for insulin secretory granules. Both crinosome-enriched and granule-enriched pellets were taken up in 1×DPBS, snap frozen and stored at −80° C. The contents of these intracellular compartments were released by thawing on ice and addition of proteinase inhibitor (cOmplete™, Roche, Switzerland) and this freeze-thaw cycle was repeated for a total of five times.

Proteins and fragments obtained in (i) secreted supernatants and (ii) intracellular granules were purified by C18 reverse-phase resin (Waters, U.S.) wetted with 50% Acetonitrile (ACN)/50% ddH2O, equilibrated with 0.1% Trifluoroacetic acid (TFA)/99.9% ddH2O and rinsed with 2% ACN/0.1% TFA/97.9% ddH2O, before sample (adjusted to a final concentration of 0.2% TFA) was loaded onto the C18 column. Sample was washed with 2% ACN/0.1% TFA/97.9% ddH2O, proteins and -fragments were eluted with 80% ACN/0.1% TFA/19.9% ddH2O, and dried using a vacuum centrifuge concentrator. Dried samples were resuspended in 2% ACN/0.1% formic acid/97.9% ddH2O. Chromatographic separation was performed using an Ultimate 3000 NanoLC system (ThermoFisherScientific, UK). Peptides were resolved by reversed phase chromatography on a 75 μm*50 cm C18 column using a linear liquid chromatography gradient of water in 0.1% formic acid (A) and 80% acetonitrile in 0.1% formic acid (B). The gradient was delivered to elute the peptides at a flow rate of 300 nl/min from 2% B to 50% B over 65 min. The eluate was ionised by electrospray ionisation using an Orbitrap-Fusion-Lumos (ThermoFisherScientific, UK) operating under Xcalibur v4.1. The instrument was programmed to acquire using a "Universal" method by defining a 3 s cycle time between a full MS scan and MS/MS fragmentation. MS/MS data was analysed using PeaksStudio (version 7.5; Bioinformatics Solutions, Canada) against the current version of the reviewed Swissprot *Homo sapiens* database downloaded from Uniprot (www.uniprot.org/uniprot/).

ELISPOT Assay

ELISPOT assays were carried out using human peripheral blood mononuclear cells (PBMCs) isolated from fresh heparinized blood. Informed consent was acquired from all participants. $1×10^6$ PBMCs divided equally over 3 wells of a 96-well plate were stimulated for 48 hours with human proinsulin B30-C13 (SEQ ID NO: 1), C19-A3 (SEQ ID NO: 49), B23-C20 (SEQ ID NO: 5), B29-C11 (SEQ ID NO: 2), B29-C14 (SEQ ID NO: 4), or $C_{-1}$-$C_{14}$ (SEQ ID NO: 3) peptide (all used at 10 μg/ml and custom manufactured by ThermoFisher Scientific), or diluent only in RPMI media supplemented with 10% (w/v) human AB serum (Sigma). The cytokine secretion assay was performed using the IFN-γ, IL-17 and IL-10 ELISPOT kits (U-CyTech) according to the manufacturer's instructions and plates were analysed using an automated ELISPOT Bioreader 6000 (Bio-Sys) and relevant software. Data are expressed as the total number of spots in triplicate wells after peptide stimulation divided by the total number of spots in diluent only control wells (stimulation index [SI]) or as responder CD4 T cells/ $10^6$ PBMCs.

Statistical Analysis

All analyses were performed with GraphPad Prism 8 software, using appropriate tests as indicated.

EXAMPLE 2

Spontaneous Onset Diabetes in DR3DQ2xRIP-B7.1 Mice

Unlike the DR4xRIP-B7.1 model we described previously (Verhagen J, et al. (2018) Sci Rep 8(1): 14106), which does not show spontaneous insulitis or diabetes, DR3DQ2xRIP-B7.1 mice develop diabetes spontaneously (FIG. 1a). Although both models demonstrate relatively high baseline levels of blood glucose at any age, only DR3DQ2xRIP-B7.1 mice develop levels>16.7 mmol/l in addition to glycosuria. By the age of 35 weeks, 46% of all animals monitored (26 out of 56) had developed autoimmune diabetes. In male and female animals, disease incidence (16/32 versus 10/24 resp.) and mean age of onset (24.2 weeks±7.3 (SD) versus 24.8±8.5 resp.) were similar. No obvious signs of other immune-mediated conditions, as evidenced by splenomegaly, cachexia, lethargy or dermal/ocular abnormalities, were detected. All mice with diabetes demonstrated severe immune infiltrate in the pancreatic islets. This infiltrate was highly diverse, with both lymphoid and myeloid cells, expressing CD4, CD8, B220, CD11b and CD11c, found in abundance in all islets (FIG. 1b). Ly6G$^+$ granulocytic cells were found in lower numbers in some islets. No notable immune cell infiltration was observed in non-diabetic mice that we examined histologically at the age of 6-8 weeks (n=5), 10 weeks (n=10), 12 weeks (n=7), 16-20 weeks (n=5) or even 35 weeks (n=13), bar one 6-week-old male where moderate infiltration of some islets was detected. This suggests that the insulitic phenotype is pathological, leads to rapid progression towards diabetes, and strongly associates with disease. Because the onset of type 1 diabetes in human HLADR3-DQ2 patients is characterised by the presence of autoantibodies against GAD65 and insulin in a majority, sera of mice were tested for antibodies against murine 30-mer peptides that span the length of murine proinsulin-2, the isoform most similar to human proinsulin, and against human GAD65, which has over 95% sequence homology with the murine equivalent. As depicted in FIG. 1c-d, there was a significant increase in the levels of anti-proinsulin-2, but not anti-GAD65, antibodies when groups of mice at increasing ages were compared.

EXAMPLE 3

Proinsulin is a Diabetogenic Antigen in DR3DQ2xRIP-B7.1 Mice

The spontaneous onset of diabetes in mice carrying a high-risk transgenic HLA suggests that an autoimmune process is central to disease development and prompted us to address the question of whether particular autoantigens are disease drivers. The hypothesis that priming animals against candidate molecules using adjuvant would accelerate disease progression if the antigens had "driver" properties was tested. Accordingly, mice were primed with either individual 30-mer peptides that overlap and span the length of murine proinsulin-2; recombinant human GAD65; the 377-amino acid intracellular region of human Islet Antigen-2 (IA-2), or PBS alone in TiterMax Gold adjuvant (FIG. 2a-f). Importantly, of these conditions, only priming with proinsulin peptides clearly hastened diabetes onset and increased incidence beyond that observed with control stimuli or through spontaneous onset. This was an unexpected finding. Previous studies have predominantly identified GAD65 and IA-2 to be the target islet antigens recognised by CD4$^+$ T cells or T cell clones from subjects with type 1 diabetes using the HLA-DR3 and -DQ2 restriction elements (Di Lorenzo T P, et al. (2007) Clin Exp Immunol 148(1): 1-16.). Moreover, the Environmental Determinants of Diabetes in the Young study suggests that anti-GAD65 autoantibodies are typically the first to appear in disease-susceptible individuals with the HLA-DR3-DQ2 haplotype. In contrast, anti-insulin autoantibodies usually emerge first in at-risk subjects with the HLA-DR4-DQ8 haplotype (Krischer J P et al. (2017) Diabetes Care 40(9): 1194-1202 and Krischer J P, et al. (2015) Diabetologia 58(5): 980-987). These represent potentially important disease endotypes, characterised by distinct pathological processes involving loss of immunological tolerance to GAD65 and insulin, respectively. In light of this, it might have been predicted that GAD65 would be the most potent antigenic driver of disease in the new DR3DQ2xRIP-B7.1 model, and yet this turned out not to be the case.

By the end of the 20-week experiment, every mouse primed with proinsulin peptides in adjuvant (10/10) had developed diabetes (mean time of onset 77±38.6 (SD) days post prime). The pancreatic immune infiltrate was not different in intensity or diversity in these antigen-challenged animals than observed in mice with spontaneous diabetes (not shown). These findings show the importance of immune recognition of proinsulin in the context of HLA-DR3-DQ2 as a diabetes-driving event in this model.

EXAMPLE 4

A Specific Region of Proinsulin is Responsible for Diabetes Induction in this Model The inventors next examined whether there is a dominant region of proinsulin that interacts in DR3DQ2xRIP-B7.1 mice to promote diabetes by repeating these adjuvanted priming experiments with each of the four proinsulin-2 peptides individually (FIG. 3a-f). Priming with B23-C20 peptide provided the most overt disease exacerbation, with very rapid development of diabetes (100% incidence by day 84 post prime, mean onset 49±16.2 (SD) days post prime). In contrast, the remaining three peptides showed disease incidences not markedly different to that expected spontaneously.

The inventors next wanted to find the core sequence in B23-C20 that mediates the antigen-primed disease acceleration (APDA) effect. One methodical approach to addressing this is to make multiple peptides across the region of interest, offset by 1 amino acid. However, several hundred potential options of any suitable length would need to be tested in this approach requiring many thousands of mice to test in correctly powered studies. The inventors therefore used an innovative step to identify the driver region of B23-C20.

Beta cells were examined to specifically identify whether there are fragments of C-peptide that are generated naturally (or whether in fact the C-peptide is always generated intact). From this, it could be established what peptide species exist naturally from the B23-C20 region and could be drivers of disease in vivo.

The inventors purified different types of granules from human beta cells (n=6 total samples) and used mass spectrometry to examine the contents.

Table 1 below shows peptides in the region of interest (from B23 through the C-peptide) in human beta cell granules:

No peptides exist that comprise residues from both the B chain and C-peptide. The reason for this is the very high efficiency of PC1/3 (proprotein convertase 1, also known as prohormone convertase; and prohormone convertase 3, or neuroendocrine convertase 1 and often abbreviated as PC1/3) which cleaves R:R in the sequence B23-C20 as part of the normal processing of the prohormone proinsulin into insulin and C-peptide. The first species in the sequence that is actually generated in vivo starts at proinsulin residue 32 (REA). Thus in some situations the N-terminal R remains. Furthermore, there are numerous sub-sequences of the C-peptide generated by beta cells. These could bind directly to HLA-DR3/DQ2 without the need for conventional antigen processing, engage with T cells and drive disease.

Then, in order to further examine how translational the mouse findings might be and understand potential interactions of driver antigens/epitopes with HLA, the inventors aligned the relevant regions of murine proinsulin-2 and human proinsulin (FIG. 4a). The B23-C20 regions of human proinsulin and murine proinsulin-2 show high homology with 23/30 amino acids (77%) identical and a further 3/30 (10%) similar between species. Next, in order to further pinpoint the region that has the dominant disease-inducing effect, 6 overlapping 14/15-mer peptides that span the length of B23-C20 were generated. Sequences with N-terminal glutamine (Q) or glutamic acid (E) residues were avoided, to obviate formation of pyroglutamic acid, yielding peptides with unpredictable properties. One of the sequences, RG-15, was highly insoluble in aqueous solution (although soluble in dimethyl sulfoxide). It has an identical predicted binding core to that of ME-15 for both HLA-DR3 and HLA-DQ2 (FIG. 4b). Based on the predicted binding affinity, none of the 14/15-mer peptides were classed as strong binders to

| C-peptide 57-87 Peptide | SEQ ID NO: | start | end | % identification in human samples (n = 6) |
|---|---|---|---|---|
| REAEDLQVGQVELGGGPGAGSLQPL | 31 | $C_{-1}$ | C24 | 100 |
| REAEDLQVGQVELGGGPGAGSLQPLALEGSLQ | 32 | $C_{-1}$ | C31 | 100 |
| EAEDLQVGQV | 33 | C1 | C10 | 100 |
| EAEDLQVGQVE | 34 | C1 | C11 | 100 |
| EAEDLQVGQVEL | 35 | C1 | C12 | 100 |
| EAEDLQVGQVELG | 36 | C1 | C13 | 100 |
| EAEDLQVGQVELGG | 37 | C1 | C14 | 100 |
| EAEDLQVGQVELGGGPGAGS | 38 | C1 | C20 | 100 |
| EAEDLQVGQVELGGGPGAGSLQ | 39 | C1 | C22 | 100 |
| EAEDLQVGQVELGGGPGAGSLQP | 40 | C1 | C23 | 100 |
| EAEDLQVGQVELGGGPGAGSLQPL | 41 | C1 | C24 | 100 |
| EAEDLQVGQVELGGGPGAGSLQPLA | 42 | C1 | C25 | 100 |
| EAEDLQVGQVELGGGPGAGSLQPLAL | 43 | C1 | C26 | 100 |
| EAEDLQVGQVELGGGPGAGSLQPLALE | 44 | C1 | C27 | 100 |
| EAEDLQVGQVELGGGPGAGSLQPLALEG | 45 | C1 | C28 | 100 |
| EAEDLQVGQVELGGGPGAGSLQPLALEGS | 46 | C1 | C29 | 100 |
| EAEDLQVGQVELGGGPGAGSLQPLALEGSL | 47 | C1 | C30 | 100 |
| EAEDLQVGQVELGGGPGAGSLQPLALEGSLQ | 48 | C1 | C31 | 100 |

HLA-DR3 or HLA-DQ2 by the prediction tool used. Importantly, the predicted binding core and affinity for the human equivalents of the peptides was generally comparable to mouse sequences (FIG. 4c).

Adjuvanted priming with the ME-15 (B29-C11) peptide led to markedly higher disease incidence during follow up than would be expected spontaneously. Disease was also significantly accelerated compared to any of the other 14/15-mer peptides tested in this experiment (FIG. 5a-f), thus strongly suggesting that the ME-15 peptide contains the minimum core amino acid sequence that binds HLA and interacts with immune cells to drive diabetes. RG-15 can also drive disease but peptides further offset to the C-terminal (DA-15 and VD-14) cannot. Thus the extreme N-terminal region of C-peptide, including the single R, defines a region containing an antigenic driver for type 1 diabetes arising on the HLA-DR3/DQ2 background.

An additional important piece of data in the preclinical model was to show that this approach can indeed identify peptides with tolerogenic properties of potential value in human disease on the DR3/DQ2 background. The inventors induced disease using B23-C20 and looked at the tolerogenic properties of ME-15 (FIG. 6). A tolerogenic effect of the ME-15 peptide was demonstrated. Thus the peptide with the strongest disease-driver properties in this B:C junction region is also tolerogenic. This suggests that a peptide such as ME-15 with HLA-DR3/DQ2 binding properties could be important in breaking of immune tolerance and disease acceleration during the natural history of diabetes development; and could also have therapeutic potential, if given early enough and via a tolerogenic (highly soluble, non-adjuvanted) route.

The similarity between the human and murine equivalents of the proinsulin region of interest indicates that these finds are highly relevant for human treatment. In order to support this, the response of human CD4$^+$ T cells from donors with the HLA-DR3-DQ2 haplotype to the human proinsulin peptide B30-C13 was analysed. This demonstrated that HLA-DR3-DQ2 donors exhibited a greater response to B30-C13 than those that did not have this haplotype (FIG. 7). Moreover, the response to B30-C13 was greater than that to our control peptide C19-A3, which was previously demonstrated to be HLA-DR4 restricted (Arif S, et al. (2004) J Clin Invest 113(3): 451-463).

EXAMPLE 5

Five peptides were tested in new-onset patients with type 1 diabetes who are HLA-DR3/DQ2 positive (FIG. 8). Inflammatory cytokine responses were seen in response to all of the peptides, indicating that they are strongly immunogenic in T1D. Furthermore, both IFN-γ and IL-17 responses were observed which are associated with cell damage in the disease. There is also an immunoregulatory (IL-10) response in these subjects, suggesting that these peptides are tolerogenic in a T1D disease setting.

All patent and literature references cited in the present specification are hereby incorporated by reference in their entirety.

| SEQ ID NO: | Name | Sequence |
|---|---|---|
| | Sequence Listings | |
| 1 | Human B30-C13 | TRREAEDLQVGQVELG |
| 2 | Human B29-C11 (Human ME-15) | KTRREAEDLQVGQVE |
| 3 | Human C_{-1}-C14 (Human RG-15) | REAEDLQVGQVELGG |
| 4 | Human B29-C14 | KTRREAEDLQVGQVELGG |
| 5 | Human B23-C20 | GFFYTPKTRREAEDLQVGQVELGGGPGAGS |
| 6 | Mouse B23-C20 | GFFYTPMSRREVEDPQVAQLELGGGPGAGD |
| 7 | Mouse GP-15 | GFFYTPMSRREVEDP |
| 8 | Mouse YA-15 | YTPMSRREVEDPQVA |
| 9 | Mouse ME-15 | MSRREVEDPQVAQLE |
| 10 | Mouse RG-15 | REVEDPQVAQLELGG |
| 11 | Mouse DA-15 | DPQVAQLELGGGPGA |
| 12 | Mouse VD-14 | VAQLELGGGPGAGD |
| 13 | Human GP-15 | GFFYTPKTRREAEDL |
| 14 | Human YA-15 | YTPKTRREAEDLQVG |
| 15 | Human DA-15 | DLQVGQVELGGGPGA |
| 16 | Human VD-14 | VGQVELGGGPGAGS |
| 17 | Mouse HLA-DR3 and HLA-DQ2 GP-15 Core | FFYTPMSRR |

-continued

| | | |
|---|---|---|
| Sequence Listings | | |
| SEQ ID NO: | Name | Sequence |
| 18 | Mouse HLA-DR3 YA-15 Core | REVEDPQVA |
| 19 | Mouse HLA-DR3 ME-15 and RG-15 Core | EVEDPQVAQ |
| 20 | Mouse HLA-DR3 and DQ2 DA-15 Core | PQVAQLELG |
| 21 | Mouse HLA-DR3 and HLA-DQ2 VD-14 Core | LELGGGPGA |
| 22 | Mouse HLA-DQ2 YA-15 Core | MSRREVEDP |
| 23 | Mouse HLA-DQ2 ME-15 and RG-15 Core | EDPQVAQLE |
| 24 | Human HLA-DR3 GP-15 Core | FFYTPKTRR |
| 25 | Human HLA-DR3 and HLA-DQ2 YA-15 Core | TRREAEDLQ |
| 26 | Human HLA-DR3 ME-15 Core | EAEDLQVGQ |
| 27 | Human HLA-DR3 RG-15 and DA-15 and HLA-DQ2 DA-15 Core | LQVGQVELG |
| 28 | Human HLA-DR3 and HLA-DQ2 VD-14 Core | VELGGGPGA |
| 29 | Human HLA-DQ2 GP-15 Core | KTRREAEDL |
| 30 | Human HLA- DQ2 ME-15 and RG-15 Core | EDLQVGQVE |
| 31 | Human Granule | REAEDLQVGQVELGGGPGAGSLQPL |
| 32 | Human Granule | REAEDLQVGQVELGGGPGAGSLQPLALEGSLQ |
| 33 | Human Granule | EAEDLQVGQV |
| 34 | Human Granule | EAEDLQVGQVE |
| 35 | Human Granule | EAEDLQVGQVEL |
| 36 | Human Granule | EAEDLQVGQVELG |
| 37 | Human Granule | EAEDLQVGQVELGG |
| 38 | Human Granule | EAEDLQVGQVELGGGPGAGS |
| 39 | Human Granule | EAEDLQVGQVELGGGPGAGSLQ |
| 40 | Human Granule | EAEDLQVGQVELGGGPGAGSLQP |
| 41 | Human Granule | EAEDLQVGQVELGGGPGAGSLQPL |
| 42 | Human Granule | EAEDLQVGQVELGGGPGAGSLQPLA |
| 43 | Human Granule | EAEDLQVGQVELGGGPGAGSLQPLAL |
| 44 | Human Granule | EAEDLQVGQVELGGGPGAGSLQPLALE |
| 45 | Human Granule | EAEDLQVGQVELGGGPGAGSLQPLALEG |
| 46 | Human Granule | EAEDLQVGQVELGGGPGAGSLQPLALEGS |
| 47 | Human Granule | EAEDLQVGQVELGGGPGAGSLQPLALEGSL |

-continued

| Sequence Listings | | |
|---|---|---|
| SEQ ID NO: | Name | Sequence |
| 48 | Human Granule | EAEDLQVGQVELGGGPGAGSLQPLALEGSLQ |
| 49 | Human C19-A3 | GSLQPLALEGSLQKRGIV |

The invention claimed is:

1. A method of treatment of Type 1 Diabetes (T1 D) comprising administering to a patient with T1 D or a non-diabetic individual identified as being at high-risk of T1 D wherein the patient has a Human Leukocyte Antigen (HLA) DR isotype 3 (DR3)-DQ2 haplotype a pharmaceutically acceptable composition comprising a peptide having at least 90% homology to the amino acid sequence of SEQ ID NO:1, SEQ ID NO: 2, SEQ ID NO: 3, SEQ ID NO: 4 or SEQ ID NO: 5, or a peptide combination thereof, and one or more pharmaceutically acceptable excipients.

2. The method of treatment of claim 1, wherein the peptide has at least 95% homology to the amino acid sequence of SEQ ID NO: 1, SEQ ID NO: 2, SEQ ID NO: 3, SEQ ID NO: 4 or SEQ ID NO: 5.

3. The method of treatment of claim 1, wherein the peptide has the amino acid sequence of SEQ ID NO: 1, SEQ ID NO: 2, SEQ ID NO: 3, SEQ ID NO: 4 or SEQ ID NO: 5.

4. The method of treatment of claim 1, wherein the peptide has the amino acid sequence of SEQ ID NO: 1 or SEQ ID NO: 2.

5. The method of treatment of claim 1, wherein the pharmaceutically acceptable composition, further comprises cysteine.

6. The method of treatment of claim 1, wherein the peptide or peptide combination is coated on a nanoparticle.

7. The method of treatment of claim 6, wherein the peptide or peptide combination is coated on the nanoparticle by being bound to a major histocompatibility (MHC) complex which is attached to the nanoparticle.

8. The method of treatment of claim 1, comprising administering the pharmaceutically acceptable composition parenterally, orally or topically.

9. The method of treatment of claim 8, comprising administering the pharmaceutically acceptable composition intradermally.

10. The method of treatment of claim 8, wherein the pharmaceutically acceptable composition is administered intravenously, intradermally, intramuscularly, subcutaneously, intraperitoneally, nasally, orally or epicutaneously.

11. The method of treatment of claim 1, comprising administering the pharmaceutically acceptable composition to a patient with a beta cell mass.

* * * * *